United States Patent
Kawamura et al.

(10) Patent No.: US 7,476,544 B2
(45) Date of Patent: Jan. 13, 2009

(54) METHOD OF JUDGING HOMOGENIZATION/REACTION COMPLETION AND METHOD OF MEASURING SOLUTION CONCENTRATION USING THE SAME

(75) Inventors: Tatsurou Kawamura, Kyotanabe (JP); Akihito Kamei, Yawata (JP)

(73) Assignee: Panasonic Corporation, Osaka (JP)

( * ) Notice: Subject to any disclaimer, the term of this patent is extended or adjusted under 35 U.S.C. 154(b) by 760 days.

(21) Appl. No.: 10/507,313

(22) PCT Filed: Mar. 12, 2003

(86) PCT No.: PCT/JP03/02962

§ 371 (c)(1),
(2), (4) Date: Sep. 10, 2004

(87) PCT Pub. No.: WO03/076913

PCT Pub. Date: Sep. 18, 2003

(65) Prior Publication Data

US 2005/0101028 A1 May 12, 2005

(30) Foreign Application Priority Data

Mar. 13, 2002 (JP) ............................ 2002-068832

(51) Int. Cl.
*G01N 21/75* (2006.01)
*G01N 21/47* (2006.01)

(52) U.S. Cl. .................. 436/164; 436/63; 422/82.05; 422/82.09; 422/82.08; 422/82.11

(58) Field of Classification Search ................. 436/164, 436/63

See application file for complete search history.

(56) References Cited

U.S. PATENT DOCUMENTS

| | | | | |
|---|---|---|---|---|
| 5,464,775 A | * | 11/1995 | Smith | ............................ 436/63 |
| 5,534,441 A | | 7/1996 | Miyazaki et al. | |
| 5,807,525 A | * | 9/1998 | Allen et al. | .................. 422/131 |

FOREIGN PATENT DOCUMENTS

| | | |
|---|---|---|
| EP | 1 022 557 A1 | 7/2000 |
| EP | 1 096 248 A2 | 5/2001 |
| EP | 1 111 368 A1 | 6/2001 |
| EP | 1 113 270 A2 | 7/2001 |
| JP | 63-053448 | 3/1988 |
| JP | 63-175749 | 7/1988 |
| JP | 9-274041 | 10/1997 |
| JP | 11-064340 | 3/1999 |
| WO | WO 03/010513 A1 | 2/2003 |

OTHER PUBLICATIONS

European Search Report issued in European Patent Application No. EP 03 70 8571, mailed Oct. 19, 2007.

* cited by examiner

*Primary Examiner*—Walter D Griffin
*Assistant Examiner*—Christine T Mui
(74) *Attorney, Agent, or Firm*—McDermott Will & Emery LLP

(57) ABSTRACT

It is intended to provide a method for determining homogenization and/or reaction completion, capable of making the measurement time necessary and sufficient and enhancing the measurement speed, and a method for measuring solution concentration using the same. According to the method for determining homogenization and/or reaction completion and the method for measuring solution concentration using the same, homogenization and reaction completion are determined based on the optical property of the liquid mixture of a test liquid and a reagent liquid.

12 Claims, 16 Drawing Sheets

Injection of pure water
Elapsed time (second)

F I G. 1 0
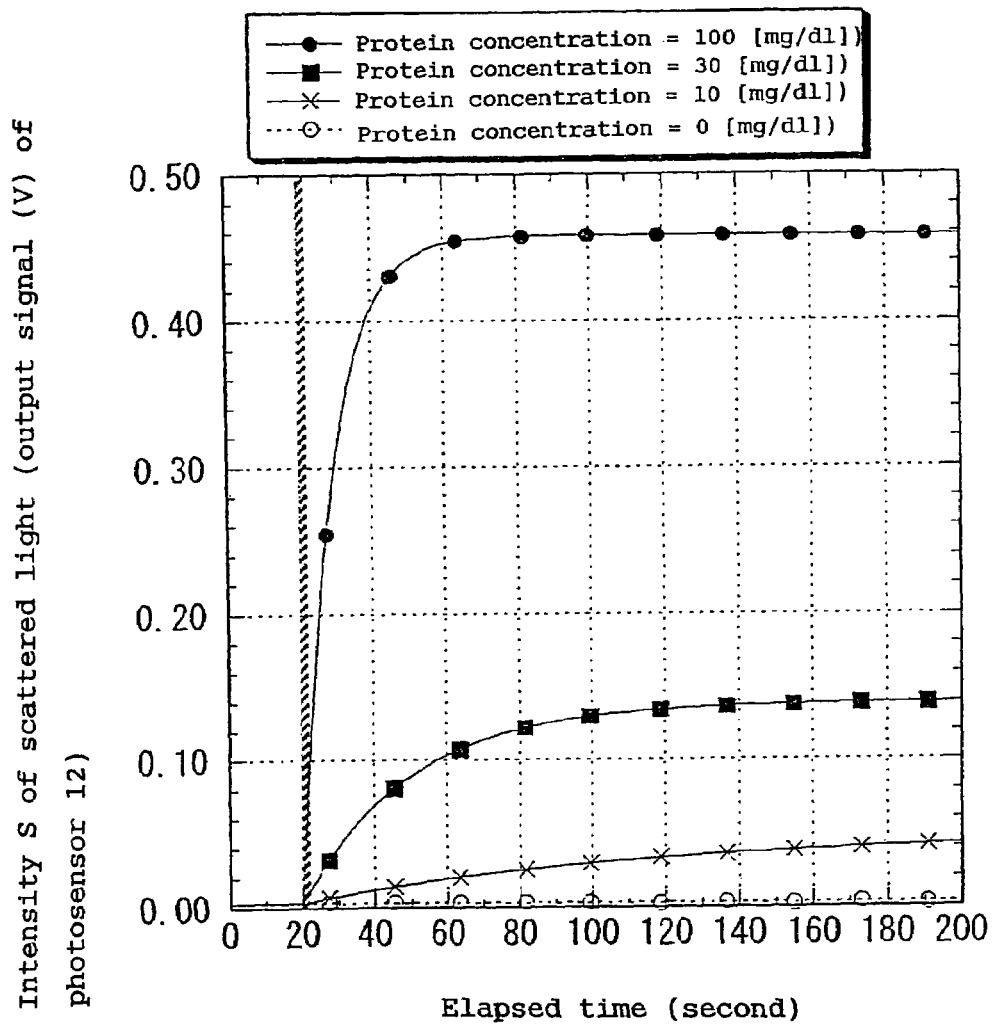

F I G. 1 2
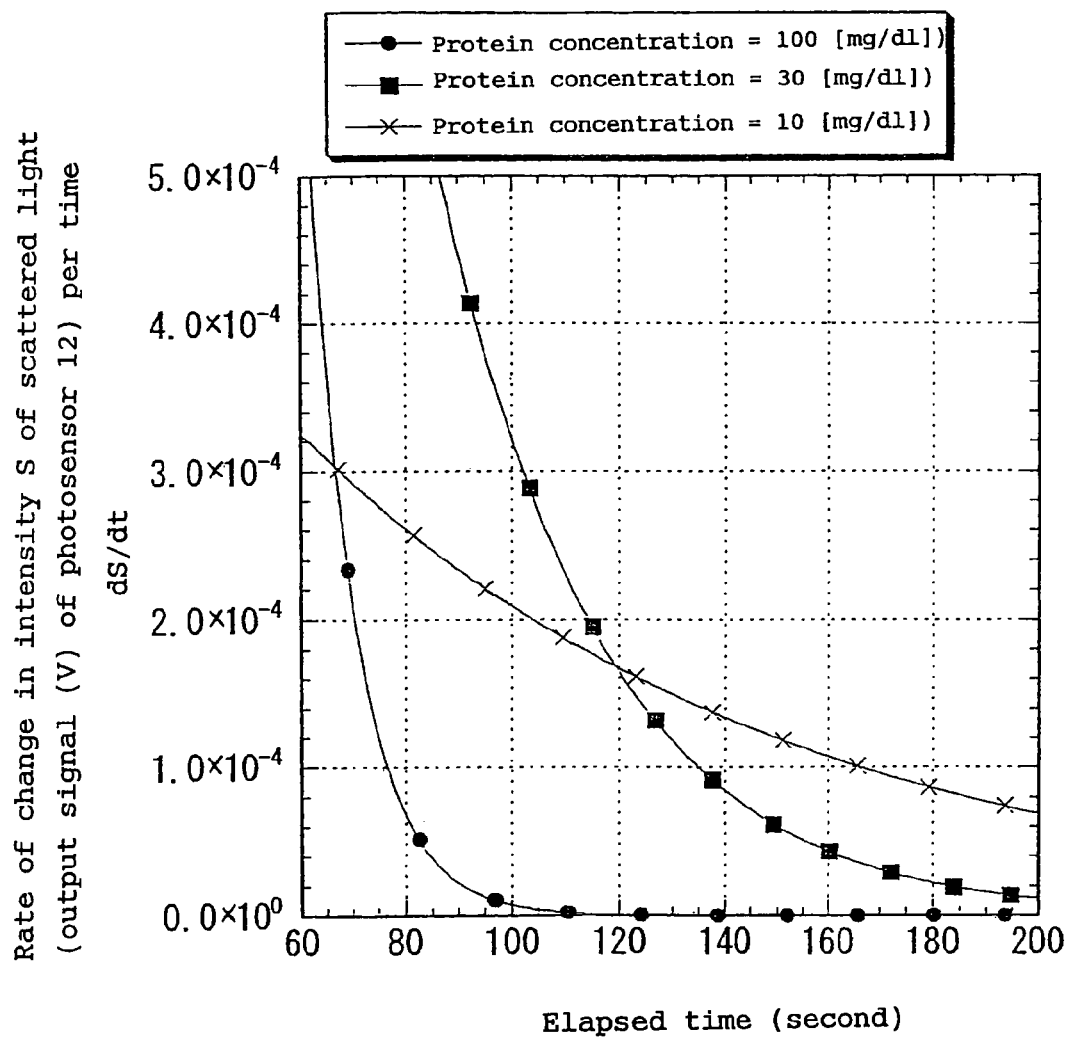

F I G. 1 5
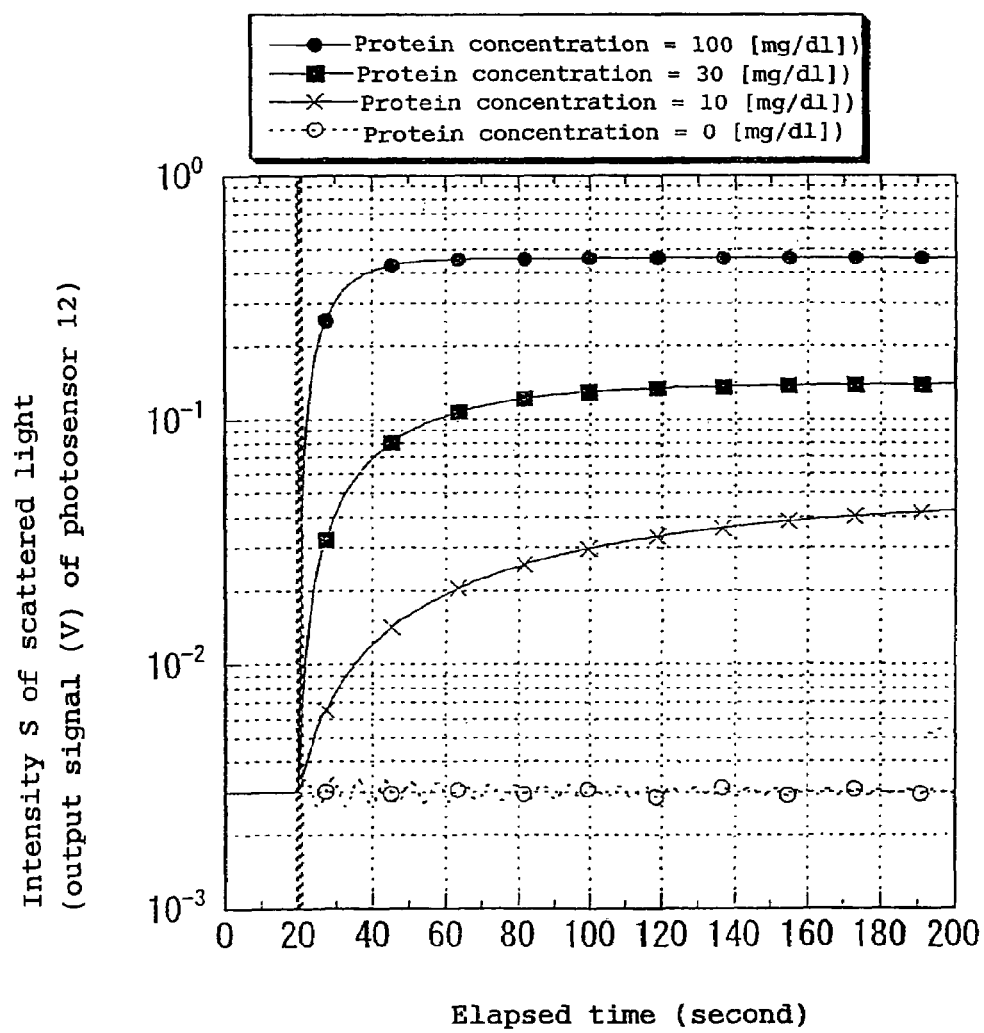

METHOD OF JUDGING HOMOGENIZATION/REACTION COMPLETION AND METHOD OF MEASURING SOLUTION CONCENTRATION USING THE SAME

TECHNICAL FIELD

The present invention relates to solution concentration measuring methods and solution concentration measuring apparatuses for determining the concentration of a solute dissolved in a test liquid, for example, protein. More specifically, the present invention measures the concentration of a specific component contained in a test liquid, by mixing a reagent liquid into the test liquid to change the optical property of the test liquid deriving from only the specific component. Particularly, by mixing the test liquid and the reagent liquid to coagulate the protein component, and detecting the decrease in light transmitted through the test liquid after the mixing and/or the increase in the intensity of light scattered during the propagation through the test liquid, the present invention measures the concentration of this protein component.

The present invention determines that the test liquid and the reagent liquid have been sufficiently stirred until homogenized, when the relation between the elapsed period of time since the mixing and the intensity of light transmitted through the liquid mixture or the intensity of scattered light satisfies a predetermined condition. Also, by this, the present invention can simultaneously determine that the reaction between the test liquid and the reagent liquid has been completed. In this way, by determining homogenization and/or reaction completion, it is possible to set the measurement time necessary and sufficient, and to reduce the measurement time. In the case of not controlling the temperature of the liquid mixture of the test liquid and the reagent liquid, in particular, the present invention can realize high reliability with a necessary and sufficient measurement time and provide highly practical methods for measuring solution concentration.

BACKGROUND ART

According to conventional methods of measuring solution concentration, a test liquid and a reagent liquid are mixed in a predetermined volume ratio and sufficiently stirred until the resultant mixture becomes homogeneous, to prepare a liquid mixture. Then, the liquid mixture is stirred at a predetermined temperature, and upon the lapse of a predetermined period of time, the optical property of the liquid mixture is measured to determine the concentration. In methods of measuring the concentration of a specific component by utilizing biochemical reactions, such as enzyme reactions and antigen-antibody reactions, it is common to set the predetermined temperature to 37° C., which is close to living body temperature. It is also common to set the predetermined period of time to a period of time within which the reaction sufficiently reaches completion. Naturally, since the rate of a reaction depends on temperature, concentration, and the like, a sufficient period of time for the completion of the reaction is set in consideration of the concentration of the test liquid at the predetermined temperature.

As described above, in conventional practice, optical property is measured under conditions where the liquid mixture is sufficiently stirred until homogenized and the reaction would never fail to reach completion. That is, sufficient conditions for homogenization and reaction completion are set.

Also, with conventional apparatuses for measuring solution concentration, a test liquid is retained in a sample cell that is structured to propagate light through the test liquid. This sample cell is in the form of a rectangular parallelepiped, made of, for example, glass, and has transmission faces that are transparent. Thus, light can be propagated through the test liquid. When the test liquid and a reagent liquid are introduced into the sample cell and mixed, the sample cell is detached from the optical system for measuring optical property, and the following operations are performed.

Usually, the top part of this sample cell is open, and a predetermined volume of a test liquid is introduced from the top part using a dropper, a pipette, a syringe, or the like. Subsequently, a predetermined volume of a reagent liquid is mixed thereinto such that the volume ratio of the test liquid to the reagent liquid is constant. Thereafter, the resultant mixture is sufficiently stirred in the sample cell with a stirring stick, stirrer, or the like until it becomes homogenized, and the whole sample cell is kept at a predetermined temperature, for example, in a constant-temperature bath. After the lapse of a predetermined period of time, the sample cell is remounted onto the optical system, and the optical property of the liquid mixture in the sample cell is measured.

However, there have been problems in that conventional solution concentration measuring methods involve a large number of processes and conventional solution concentration measuring apparatuses are large-scaled. Further, there has been another problem of requiring increased measurement time. Therefore, there is a demand for solution concentration measuring apparatuses having a simple structure without a constant-temperature bath and the like, as well as solution concentration measuring methods capable of easy automation.

Further, there has also been another problem in that the processes of loading and unloading the sample cell cause a slight change in the position of the optical system, possibly leading to errors in measurement results. Furthermore, still another problem has been that complicated operations are necessary, and hence, operation mistakes, etc. tend to occur, thereby resulting in poor reliability.

In consideration of the above-mentioned problems, an object of the present invention is to provide a highly reliable method of measuring solution concentration capable of easy automation, as well as a highly reliable, small-sized apparatus of measuring solution concentration capable of easy automation. The present invention further provides a solution concentration measuring method and a solution concentration measuring apparatus which can reduce the time necessary for homogenization and/or reaction completion to the requisite minimum, thereby enabling a reduction in measurement time.

DISCLOSURE OF INVENTION

The present invention relates to a method for determining homogenization and/or reaction completion, including the steps of: (1) mixing a test liquid and a reagent liquid to obtain a liquid mixture; (2) measuring an optical property of the liquid mixture after the mixing continuously or a plurality of times discretely; (3) obtaining a relation between the measured value of the optical property obtained and the elapsed period of time since the start of the measurement after the mixing; and (4) determining, on the basis of the relation, whether the test liquid and the reagent liquid have been substantially homogeneously mixed with each other and/or a reaction between the test liquid and the reagent liquid has been substantially completed. The steps (1) to (4) are performed in this order.

In this method for determining homogenization and/or reaction completion, the step (3) is preferably a step of obtaining $dS1/dt$ (wherein S1 is the measured value of the optical property obtained and T is the elapsed period of time since the start of the measurement after the mixing), and the step (4) is preferably a step of determining that the test liquid and the reagent liquid have been substantially homogeneously mixed with each other and/or the reaction between the test liquid and the reagent liquid has been substantially completed, when the $dS1/dt$ has continuously been in a predetermined range R1 for a predetermined period of time T1 or longer.

Also, the step (3) is preferably a step of obtaining $(dS1/dt)/S1$ (wherein S1 is the measured value of the optical property obtained and T is the elapsed period of time since the start of the measurement after the mixing), and the step (4) is preferably a step of determining that the test liquid and the reagent liquid have been substantially homogeneously mixed with each other and/or the reaction between the test liquid and the reagent liquid has been substantially completed, when the $(dS1/dt)/S1$ has continuously been in a predetermined range R2 for a predetermined period of time T2 or longer.

Further, the present invention pertains to a method for determining homogenization and/or reaction completion, including the steps of: (1) mixing a test liquid and a reagent liquid to obtain a liquid mixture; (2) measuring an optical property of the test liquid and the liquid mixture continuously, or, measuring an optical property of the test liquid at least once and measuring an optical property of the liquid mixture after the mixing a plurality of times discretely; (3) obtaining a relation between the measured value of the optical property obtained and the elapsed period of time since the start of the measurement after the mixing; and (4) determining, on the basis of the relation, that the test liquid and the reagent liquid have been substantially homogeneously mixed with each other and/or the reaction between the test liquid and the reagent liquid has been substantially completed. The steps (1) to (4) are performed in this order.

In the method for determining homogenization and/or reaction completion, the step (3) is preferably a step of obtaining $(dS1/dt)/(S1-S0)$ (wherein S0 is the measured value of the optical property of the test liquid, S1 is the measured value of the optical property of the liquid mixture, and T is the elapsed period of time since the start of the measurement after the mixing), and the step (4) is preferably a step of determining that the test liquid and the reagent liquid have been substantially homogeneously mixed with each other and/or the reaction between the test liquid and the reagent liquid has been substantially completed, when the $(dS1/dt)/(S1-S0)$ has continuously been in a predetermined range R3 for a predetermined period of time T3 or longer.

Furthermore, the present invention is directed to a method for measuring solution concentration, wherein the homogenization of the mixture of the test liquid and the reagent liquid and/or the substantial completion of the reaction therebetween are determined according to the above-mentioned method for determining homogenization and/or reaction completion, and then the concentration of a specific component of the test liquid is determined based on the measured value S1 or the measured values of S0 and S1.

This method for measuring solution concentration preferably includes the step of mixing another reagent liquid with the test liquid, after determining that the test liquid and the reagent liquid have been homogeneously mixed and/or the reaction therebetween has been substantially completed.

In this case, preferably, another reagent liquid is mixed with the test liquid upon the lapse of a predetermined period of time T4 after determining that the test liquid and the reagent liquid have been homogeneously mixed and/or the reaction therebetween has been substantially completed, and the optical property of the liquid mixture is measured prior to the lapse of the predetermined period of time T4.

The present invention also relates to an apparatus for measuring solution concentration, including: a light source that irradiates a test liquid with light; a sample cell that retains the test liquid; a photosensor 1 that detects light transmitted through the test liquid and/or a photosensor 2 that detects light scattered while the light is propagated through the test liquid; and a computer that analyzes an output signal of the photosensor 1 and/or the photosensor 2, wherein based on the above-mentioned method for measuring solution concentration, the computer analyzes the output signal of the pohotosensor 1 and/or the photosensor 2 to calculate the concentration of the test liquid.

That is, the computer preferably includes controlling means for measuring an optical property of the liquid mixture obtained by mixing a test liquid and a reagent liquid continuously or a plurality of times discretely, obtaining a relation between the measured value of the optical property obtained and the elapsed period of time since the start of the measurement after the mixing, determining, on the basis of the relation, that the test liquid and the reagent liquid have been substantially homogeneously mixed with each other and/or a reaction between the test liquid and the reagent liquid has been substantially completed, and determining the concentration of a specific component in the test liquid based on the measured value.

Also, the controlling means of the computer may measure the optical property of the test liquid and the liquid mixture continuously, or, it may measure the optical property of the test liquid at least once and measure the optical property of the liquid mixture after the mixing a plurality of times discretely.

Further, it is preferred that the apparatus for measuring solution concentration include an injector that injects a reagent liquid into the test liquid in the sample cell for mixing and that the injector be controlled by the computer or the controlling means.

In the apparatus for measuring solution concentration, it is preferred that the optical property of the test liquid be measured, using the light source, to determine the concentration of a specific component in the test liquid.

It is also preferred to perform stirring by means of the mechanical effect produced by the injection of the reagent liquid.

Further, in the above-mentioned method for determining homogenization and/or reaction completion, method for measuring solution concentration, and apparatus for measuring solution concentration, it is preferred that a measurement be rendered invalid when homogenization and/or reaction completion has not been determined within a predetermined period of time T from the start of the measurement.

It is also preferred that when the concentration of the analyte in the test liquid is the lowest possible concentration, the above-mentioned predetermined period of time T satisfy the relation $T \geqq T5$ wherein T5 is the elapsed period of time since the start of a measurement until homogenization or reaction completion is determined by the above-mentioned method for determining homogenization and/or reaction completion.

It is also preferred that the substance that reacts with the analyte be an antibody that specifically reacts and combines with the analyte and that the signal related to the optical property that derives from the specific binding reaction be the turbidity of the liquid mixture.

It is further preferred that the analyte be human albumin.

BRIEF DESCRIPTION OF DRAWINGS

FIG. 10 is a graph showing the changes over time in the output signal of a photosensor 12 in Embodiment 2 of the present invention;

FIG. 12 is a graph obtained by enlarging the ordinate around 0 and enlarging the abscissa around 60 to 200 seconds in FIG. 11;

FIG. 15 is a graph in which the ordinate of FIG. 12 is logarithmically expressed;

BEST MODE FOR CARRYING OUT THE INVENTION

The present invention relates to a solution concentration measuring method that qualitatively or quantitatively determines an analyte, by mixing a test liquid containing the analyte with a reagent liquid containing a substance that reacts with the analyte, and detecting a signal related to the optical property deriving from the reaction.

The present invention relates to a method for determining homogenization and/or reaction completion, including the steps of: (1) mixing a test liquid and a reagent liquid to obtain a liquid mixture; (2) measuring an optical property of the liquid mixture after the mixing continuously or a plurality of times discretely, or, measuring an optical property of the test liquid and the liquid mixture continuously, or, measuring an optical property of the test liquid at least once and measuring an optical property of the liquid mixture after the mixing a plurality of times discretely; (3) obtaining a relation between the measured value of the optical property obtained and the elapsed period of time since the start of the measurement after the mixing; and (4) determining, on the basis of the relation, whether the test liquid and the reagent liquid have been substantially homogeneously mixed with each other and/or a reaction between the test liquid and the reagent liquid has been substantially completed.

The present invention also provide a solution concentration measuring method and a solution concentration measuring apparatus using this method for measuring homogenization and/or reaction completion.

Referring now to drawings, various embodiments of the present invention are described below.

Embodiment 1

Figure 1:
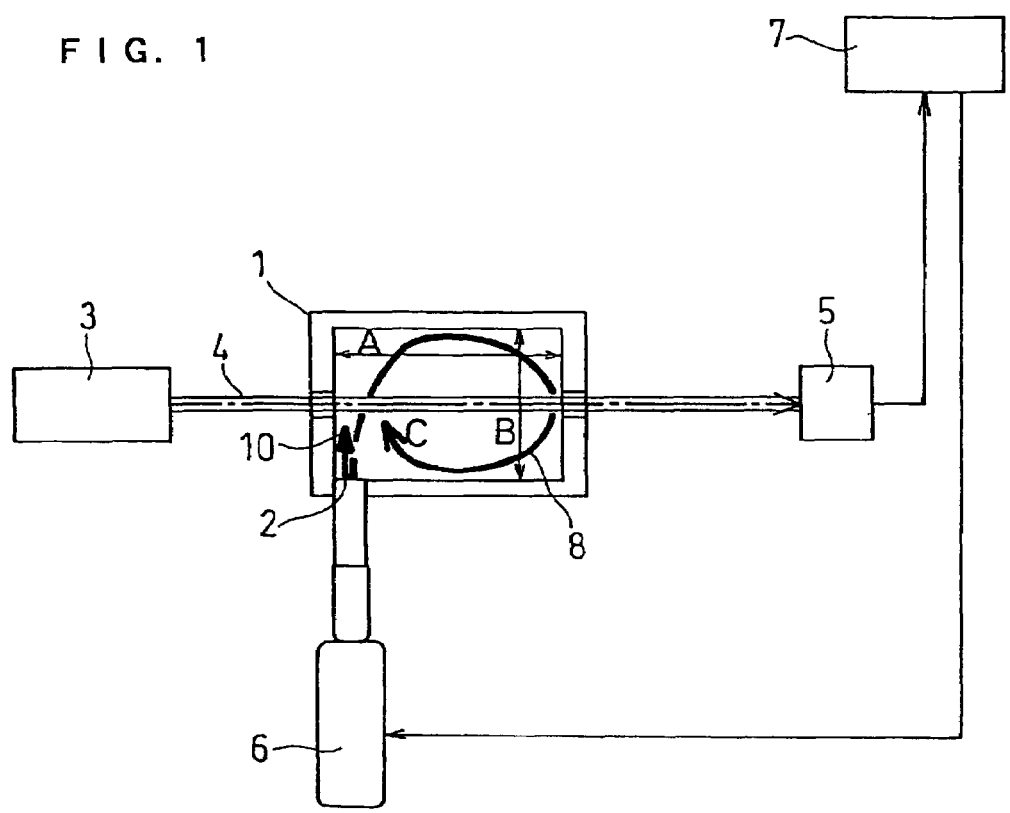
FIG. 1 is a top view of a solution concentration measuring apparatus according to Embodiment 1 of the present invention.
Figure 2:
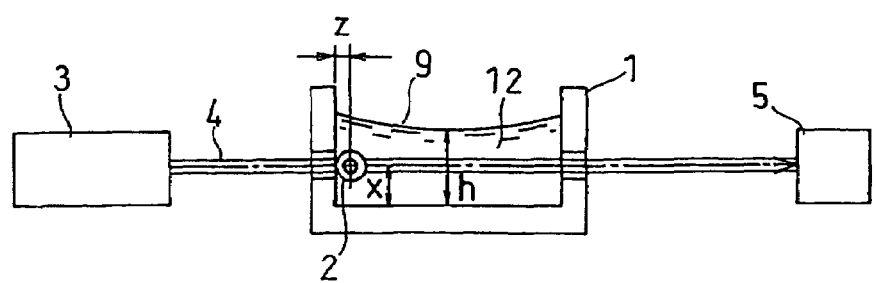
FIG. 2 is a partially cross-sectional side view of the solution concentration measuring apparatus according to Embodiment 1 of the present invention.

Referring to FIGS. 1 and 2, Embodiment 1 of the present invention is detailed below. FIG. 1 is a top view of a solution concentration measuring apparatus according to Embodiment 1 of the present invention. FIG. 2 is a partially cross-sectional side view of the solution concentration measuring apparatus according to Embodiment 1 of the present invention. In FIGS. 1 and 2, the skeletal part of a sample cell 1 is composed of an aluminum container that is in the form of a rectangular parallelepiped and has an opening at the top. A glass plate, serving as an optical window, is fitted into a pair of side faces of the sample cell 1 to form an optical path, so that light can be transmitted through a test liquid (or a liquid mixture of a test liquid and a reagent liquid) retained in the sample cell 1. In FIG. 1, the distance between the optical windows (optical length), which is the distance in the direction of light propagation in the sample cell 1, is represented by A, and the distance in the direction perpendicular to the direction of light propagation in the sample cell 1 is represented by B. In this embodiment, A and B are set to 0.8 cm and 0.4 cm, respectively, as a representative example to explain the present invention.

As illustrated in FIG. 1, an injection port 2 is provided in the edge of the side face of the sample cell 1 having no optical window, and the internal diameter (diameter) of the injection port 2 is 0.1 cm. As illustrated in FIG. 2, the center of the vertical section of the injection port 2 is positioned at a distance x from the bottom face of the sample cell 1 and at a distance z from the optical window. Injection direction 10 is parallel to the faces having the optical windows and perpendicular to the direction of light propagation. In this embodiment, x and y are set to 0.4 cm and 0.1 cm, respectively, as a representative example to explain the present invention.

A semiconductor laser module 3, which is a light source, projects substantially parallel light 4 onto the test liquid in the sample cell. The substantially parallel light 4 has a wavelength of 780 nm, an intensity of 3.0 mW, and a beam diameter of 0.2 cm. The optical axis of this substantially parallel light 4 is parallel to the bottom face of the sample cell 1 and positioned at a distance of 0.4 cm from the bottom face. Therefore, the optical axis and the injection port 2 are positioned at the same height from the bottom face, and the optical axis of the substantially parallel light 4 and the injection axis extending from the center of the section of the injection port 2 in the injection direction 10 have a point of intersection in the solution in the sample cell 1.

A photosensor 5 is a photosensor which detects light that has been transmitted through the test liquid. A pump 6 injects a reagent liquid from the injection port 2 into the test liquid in the sample cell 1. A computer 7 analyzes the output signal of the photosensor 5 and controls the pump 6. An arrow 8 schematically indicates the direction of the vortex that occurs in the sample cell 1 when the reagent liquid is injected from the injection port 2. Also, the lowest part of liquid level 9 of the test liquid is positioned at a height h from the bottom face of the sample cell 1. In the present invention, the liquid level is defined as the level that is in contact with the lowest part of the liquid level 9 and parallel to the horizontal level. According to this definition, the injection direction is parallel to the liquid level in this embodiment.

The sample cell 1 has inner wall corners that are rounded. That is, the corners of the sample cell 1 are not right-angled in a strict sense. Thus, when h=0.8 cm, the sample cell 1 contains about 0.25 ml of the test liquid.

In this embodiment, a dispersion obtained by homogeneously dispersing polystyrene fine particles having a mean diameter of 20 nm in pure water is charged into the sample cell 1 as the test liquid. The whole test liquid is homogeneously turbid.

First, the mechanism of injecting pure water into this test liquid is described. The polystyrene fine particles have a specific gravity close to that of pure water, and their particle size is also small. Thus, once they have been fully homogeneously dispersed in pure water, phenomena such as separation and precipitation do not occur during the period of time in which the method according to the present invention is carried out. However, if they have not been homogeneously dispersed due to insufficient stirring, such phenomena may occur.

When pure water is injected into this test liquid, the polystyrene fine particles diffuse therethrough, so that the concentration of the polystyrene fine particles lowers. Consequently, the degree of opacity of the whole test liquid, i.e., turbidity, lowers. This turbidity is measured as the intensity of transmitted light by detecting the output signal of the photosensor 5.

In this way, the change in the turbidity of the liquid containing fine particles due to diffusion involves no chemical reaction. Therefore, the turbidity of the whole test liquid depends solely on the degree of diffusion of the polystyrene fine particles, and hence, there is no need to take reaction speed into consideration. That is, the fact that the turbidity has been stabilized at a certain value means that the fine particles have been sufficiently spread throughout the liquid and homogeneously dispersed.

From these, observing the turbidity by mixing a liquid containing fine particles as a reagent liquid with a test liquid is convenient in verifying the stirring effect. In this embodiment, the present invention is simplified for the purpose of explanation by selecting only the result of determination of the homogenization attained by the stirring of the present invention.

The operations of this embodiment were conducted as follows:

First, the test liquid containing the polystyrene fine particles was introduced into the sample cell 1. At this time, the volume of the test liquid introduced was 0.25 ml. The computer 7 was started to measure (record) the output signal of the photosensor 5. The changes over time in the output signal of the photosensor 5 after the start of the measurement following the introduction are shown in FIG. 3.

Figure 3:
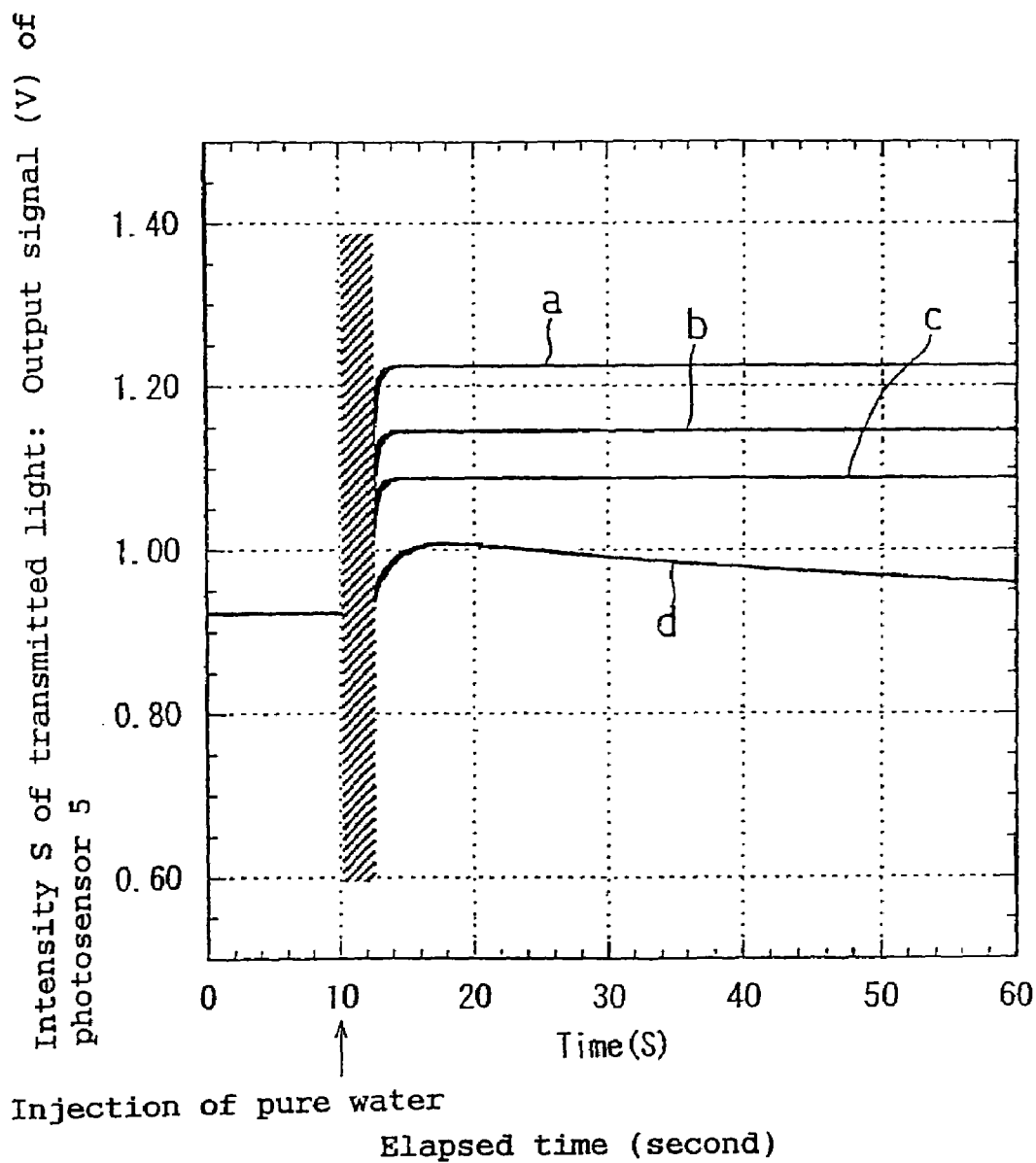
FIG. 3 is a graph showing the changes over time in the output signal of a photosensor 5 in Embodiment 3 of the present invention.

In FIG. 3, the elapsed period of time since the start of measurement of the output signal is plotted in abscissa, and the output signal of the photosensor 5 is plotted in ordinate. At an elapsed time of 10 seconds, the computer 7 controlled the pump 6 so that pure water was injected from the injection port 2 over 2 seconds. The changes in the output signal of the photosensor 5 in the case of pure water injection, as described, are shown by solid lines in FIG. 3. In FIG. 3, "a", "b", "c", and "d" show the changes in the output signal of the photosensor 5 resulting from the injection of 0.1 ml of pure water, 0.07 ml of pure water, 0.05 ml of water, and 0.03 ml of pure water, respectively.

In this figure, for 2 to 3 seconds from the start of the pure water injection, i.e., the elapsed time of 10 seconds since the start of the recording, the flux of the injected pure water itself entered the optical path of the substantially parallel light 4. As a result, the intensity and the propagation direction of transmitted light were disturbed, causing a violent change in the output signal of the photosensor 5. In FIG. 3, the amplitude of the change is illustrated as the hatched area, and the output signal changed between 0.6 to 1.4 V. Even when the same volume of pure water was injected, the amplitude of the change was shown in this area, though the details of the change were not confirmed. Since the concentration of the polystyrene particles lowered depending on the amount of pure water injected, the turbidity also decreased depending on the amount of injection.

When the injected amounts of pure water were 0.1 ml, 0.07 ml, and 0.05 ml, as shown by the solid lines "a", "b", and "c" of FIG. 3, respectively, the resultant output signals were commensurate with the respective amounts of injection, and the output signals themselves were stabilized. This is because the injection of pure water produced a vortex in the test liquid, which allowed the liquid mixture of the test liquid and the pure water to be sufficiently stirred until it became homogenized. The homogenization could also be confirmed by visual observation. On the other hand, when the amount of injection was 0.03 ml, the output signal was not stabilized, as shown by the solid line "d". This is because the liquid mixture of the test liquid and the pure water was stirred insufficiently and was not stirred until homogenized. The inconsistencies in the concentration of the polystyrene fine particles could also be confirmed by visual observation.

As described above, the solid lines "a" to "c" represented the cases where the liquid mixture of the test liquid and the pure water was sufficiently stirred until homogenized, while the solid line "d" represented the case where the liquid mixture could not be sufficiently stirred until homogenized.

Conventionally, in measuring the optical property of a test liquid, such as turbidity, from the output signal of the photosensor 5, one had to wait for the lapse of a period of time within which the output signal of the photosensor 5 became sufficiently stabilized. After the lapse of that period of time, one analyzed the output signal of the photosensor 5. For example, the output signal of the photosensor 5 at an elapsed time of 60 seconds since the start of the recording was used. In the case of the solid line "d" according to the present invention, however, an accurate measurement of the optical property was not possible, because the liquid mixture had not been homogenized. Hence, there was a need to additionally make visual observations to confirm the homogenization.

Contrary to such conventional art, the method of the present invention, which will be described below, determines whether or not the liquid mixture has been sufficiently stirred, i.e., whether or not the liquid mixture has become homogenized, based on the optical property of the liquid mixture, i.e., the output signal of the photosensor 5. Summing up, this method is an example of being able to reduce the measurement time by setting the waiting time from the start of a measurement until obtaining the result necessary and sufficient.

First, the maximum period of time within which a measurement is performed is set in advance. This period refers to the longest waiting period of time from the start of the measurement until obtaining the result, and if a measurement takes more than this maximum period of time, this measurement is rendered invalid. This pre-set period of time is referred to as a predetermined period of time T.

According to this method, homogenization is determined when the amount of change in an output signal S1 of the photosensor 5 per unit time, i.e., a derivative signal $dS1/dt$, has continuously been in a predetermined range R1 for a predetermined period of time T1 within the predetermined period of time T.

Specifically, the liquid mixture is determined as having been homogenized when $dS1/dt$ [V/S] has continuously been in a predetermined range R1 represented by formula (1) for a predetermined period of time T1 (1.5 seconds) or longer within a predetermined period of time T (60 seconds) after the start of a measurement.

$$-5\times10^{-4} \leq dS1/dt \leq 5\times10^{-4} \quad (1)$$

It should be noted that if the predetermined period of time T, which corresponds to the longest waiting period of time, is not properly set, the derivative signal $dS1/dt$ may be in the predetermined range R1 for the predetermined period of time T1, even if the liquid mixture has not been homogenized due to insufficient stirring, particularly even if pure water regions are separated from fine particle regions. Thus, there is a possibility of making a wrong determination that the liquid mixture has been homogenized.

Figure 4:
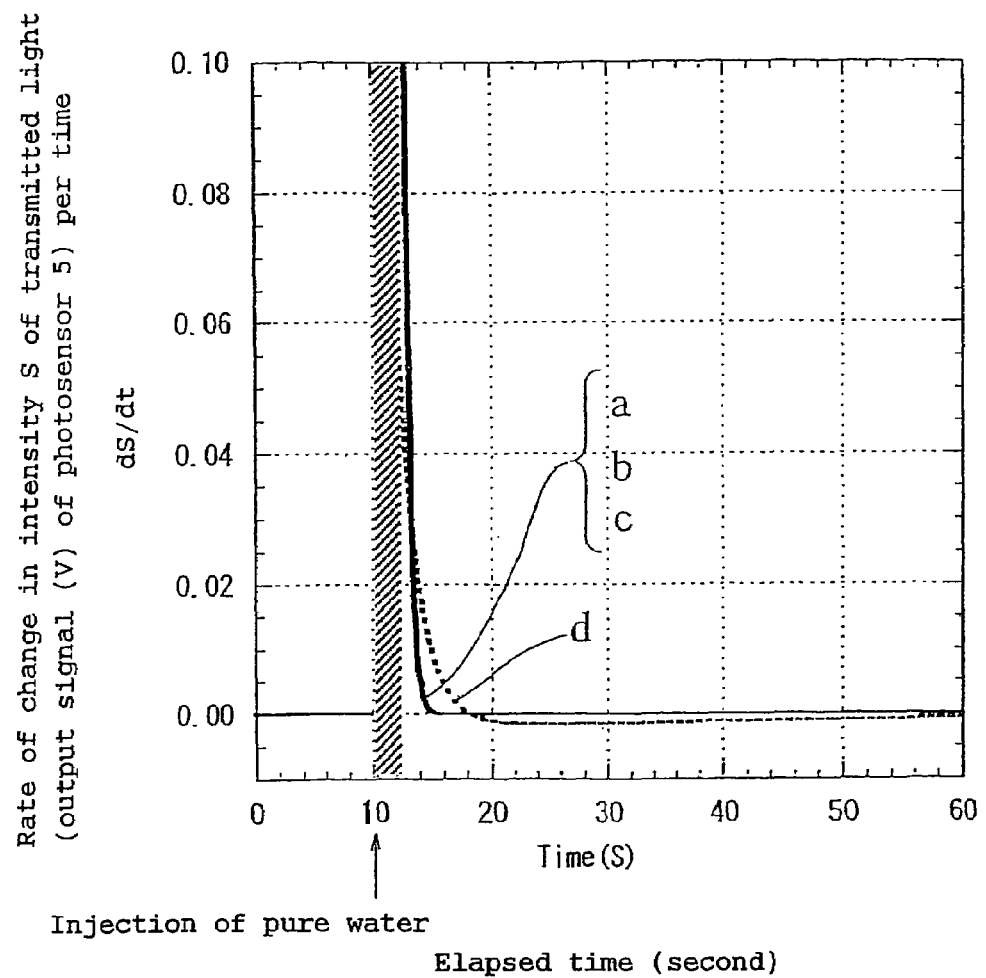
FIG. 4 is a graph showing the rate of change over time in the derivative signal of output signal of a photosensor 5 in Embodiment 1 of the present invention.
Figure 5:
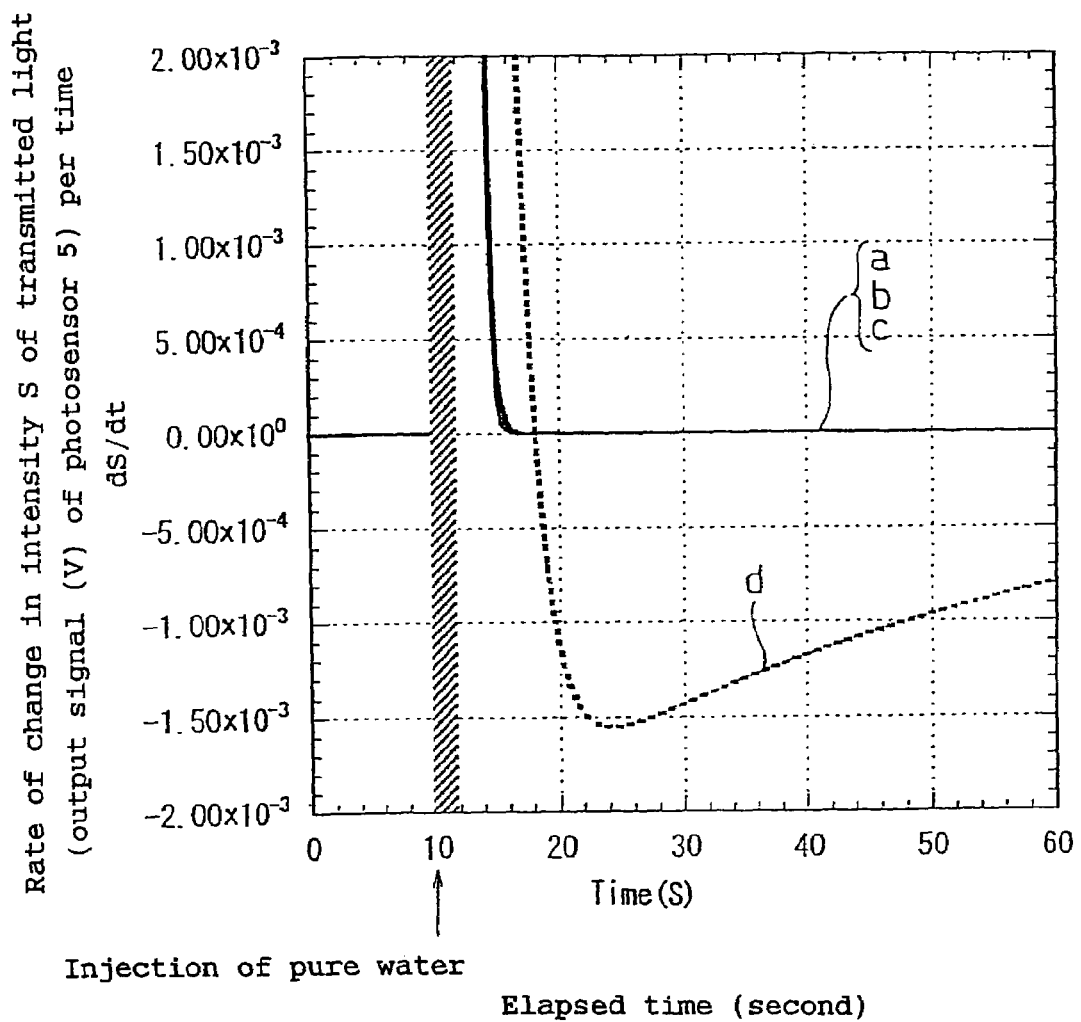
FIG. 5 is a graph obtained by enlarging the ordinate around 0 in FIG. 4.

FIG. 4 shows the derivative signal of output signal of the photosensor 5. The solid lines "a" to "d" of FIG. 3 correspond to the derivative values (dS/dt) of the signal intensities represented by the solid lines "a" to "c" and the dotted line "d" of FIG. 4, respectively. In FIG. 4, in the same manner as in FIG. 3, during the period of about 2 seconds or more from the elapsed time of 10 seconds at which the injection of pure water was started, the flux of the injected pure water itself entered the optical path of the substantially parallel light 4. As a result, the intensity and the propagation direction of transmitted light were disturbed, causing a violent change in the derivative signal of output signal of the photosensor 5. In FIG. 4, the solid lines "a" to "c" appeared to coincide with one another. Thus, a graph was prepared by enlarging the ordinate of FIG. 4 around 0 (FIG. 5). FIG. 5 showed that the solid lines "a" to "c" asymptotically approached zero, and that the broken line "d" largely swayed toward the minus side before going through the minimum value. However, in FIG. 5, the solid lines "a" to "c" also appeared to coincide with one another.

Figure 6:
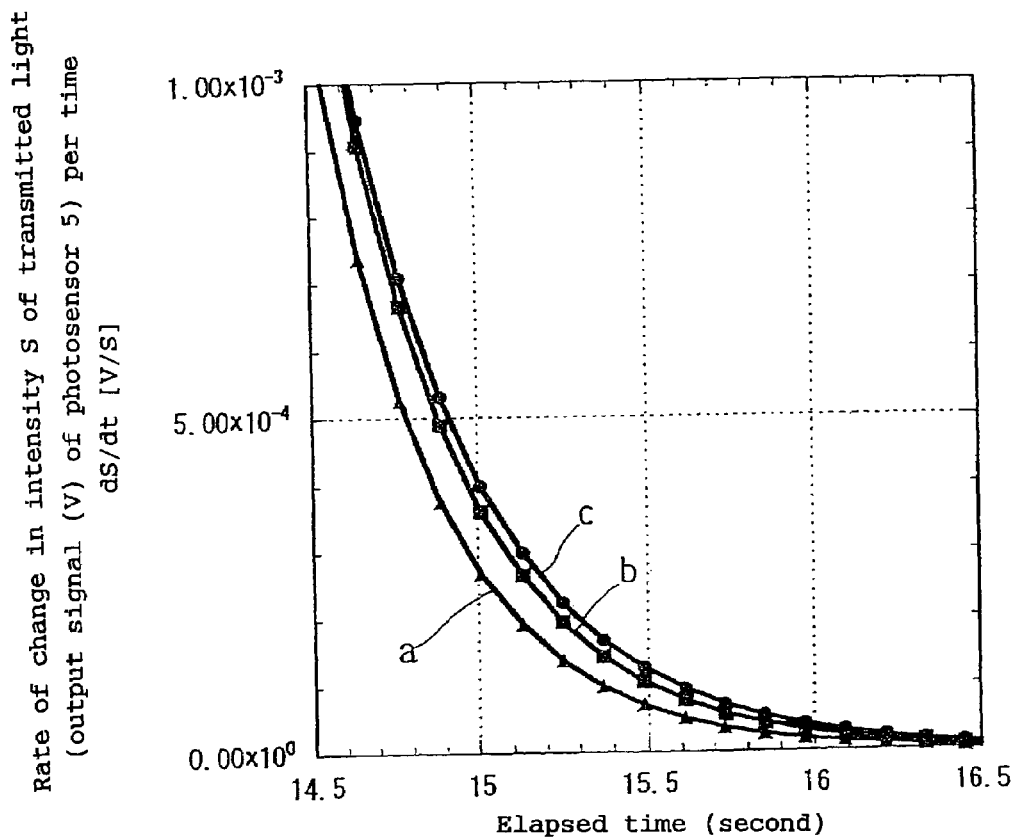
FIG. 6 is a graph obtained by enlarging the ordinate at 0 and greater and enlarging the abscissa around 14.5 to 16.5 seconds in FIG. 4.

Thus, FIG. 6 showed a graph obtained by enlarging the ordinate at zero and greater and enlarging the abscissa around 14.5 to 16.5 seconds in FIG. 4. In FIG. 6, ▲ corresponds to "a", ■ corresponds to "b", and ● corresponds to "c". As is clear from FIG. 6, "a" to "c" asymptotically approached zero.

For the condition for determining homogenization, a point of time when the derivative signal $dS1/dt$ of output signal of the photosensor 5 has continuously been in the predetermined range R1 represented by formula (1) for the predetermined period of time T1 (1.5 seconds) or longer within the predetermined period of time T (60 seconds) after the start of a measurement was found as follows.

The derivative signal $dS1/dt$ of output signal of the photosensor 5 became $5\times10^{-4}$ [V/S] or less from an elapsed time of 14.79 seconds for "a", from an elapsed time of 14.88 seconds for "b", and from an elapsed time of 14.92 seconds for "c". After these points in time, since "a" to "c" asymptotically approached zero, the derivative signal was in the predetermined range R1 as expressed by formula (1).

Therefore, in FIG. 6, if the point of the lapse of 1.5 seconds from the point when the derivative signal dS/dt fell within the predetermined range R1 expressed by formula (1) is within the predetermined period of time (T=60 seconds) from the start of the measurement, the liquid mixture could be determined as having been homogenized at an elapsed time of 15 seconds. Specifically, for "a", homogenization could be determined at an elapsed time of 16.29 seconds. For "b", homogenization could be determined at an elapsed time of 16.38 seconds. For "c", homogenization could be determined at an elapsed time of 16.42 seconds.

Figure 7:
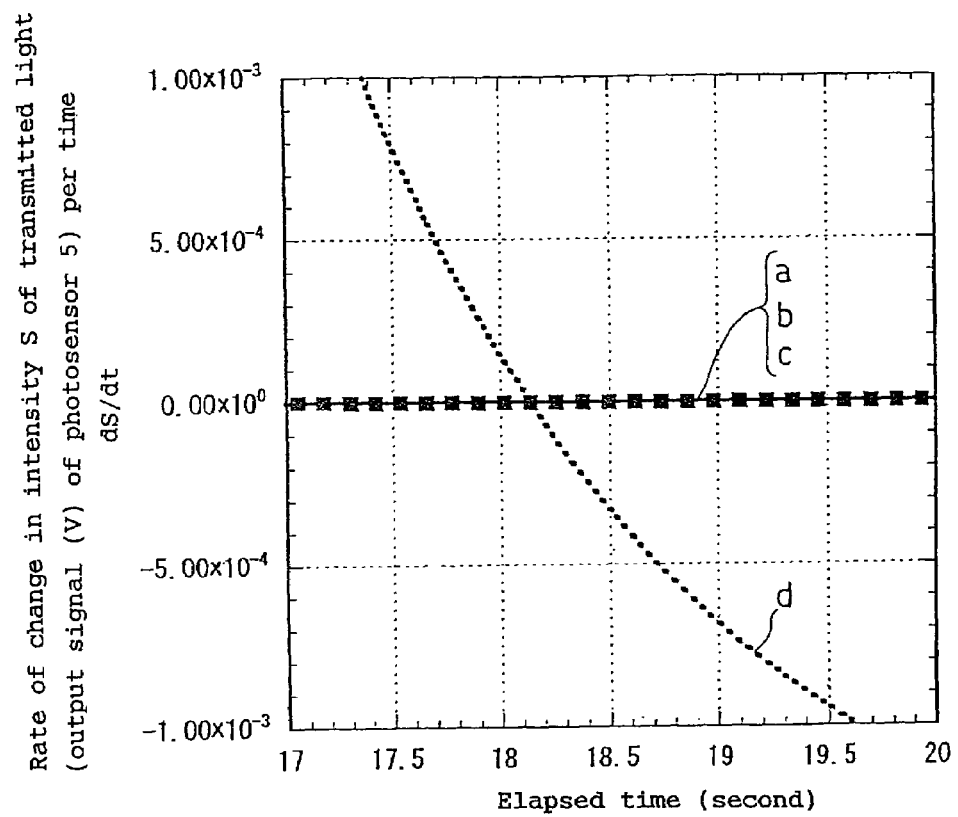
FIG. 7 is a graph obtained by enlarging the ordinate around 0 and enlarging the abscissa around 17 to 20 seconds in FIG. 4.

Meanwhile, a graph was prepared by enlarging the ordinate of FIG. 4 around 0 and enlarging the abscissa at elapsed times of 17 to 20 seconds (FIG. 7). As shown in FIG. 7, the derivative signal $dS1/dt$ of output signal of the photosensor 5 is in the predetermined range R1 expressed by formula (1) from an elapsed time of 17.69 seconds until an elapsed time of 18.71 seconds. In this case, since the derivative signal was within the R1 only for 1.02 seconds (=18.71−17.69), the liquid mixture could not be determined as having been homogenized. Also, the liquid mixture according to "d" was determined as not having been homogenized, because, as is clear from FIG. 5, the derivative signal does not fall within the range R1 at least until the point of the lapse of the predetermined period of time (T=60 seconds) after the start of the measurement. By using such determination condition, it was possible to adequately determine whether or not the liquid mixture had been sufficiently stirred and homogenized.

In measuring the optical property of a test liquid, such as turbidity, from the output signal of the photosensor 5, the output signal of the photosensor 5 at the point when homogenization was determined may be analyzed, as described above. Specifically, for "a", the output signal of the photosensor 5 at the elapsed time of 16.29 seconds may be used, and for "b", the output signal of the photosensor 5 at the elapsed time of 16.38 seconds may be used. Also, for "c", the output signal of the photosensor 5 at the elapsed time of 16.42 seconds may be used. Accordingly, the optical property can be measured in a necessary and sufficient measurement time while the accuracy is assured, so that the measurement time can be reduced. Further, misoperations due to insufficient homogenization can be avoided.

It is needless to say that the condition for determining homogenization is not limited to the above-described condition. That is, T, T1, and the predetermined range R expressed by formula (1) may be set as appropriate, according to various conditions such as the size of the fine particles, the density of the particle, the injection speed, the arrangement of the optical system, the accuracy required, the measurement time, the calibration curb, etc. Also, in calculating the concentration of a specific component of a test liquid, the computer 7 analyzes the output signal of the photosensor 5 at the point when homogenization was determined, while referring to the pre-set calibration curb, in order to calculate the concentration of the test liquid.

As described above, according to this embodiment, the degree of stirring of the liquid mixture and homogenization can be determined with the sample cell mounted on the optical system. Further, since the time needed for a measurement is necessary and sufficient, time can be saved. Accordingly, while the process can be simplified, misoperations are unlikely to occur. These practical effects are extremely large, thereby making it possible to enhance the efficiency of measurements and tests and to achieve labor-savings thereof.

Embodiment 2

Figure 8:
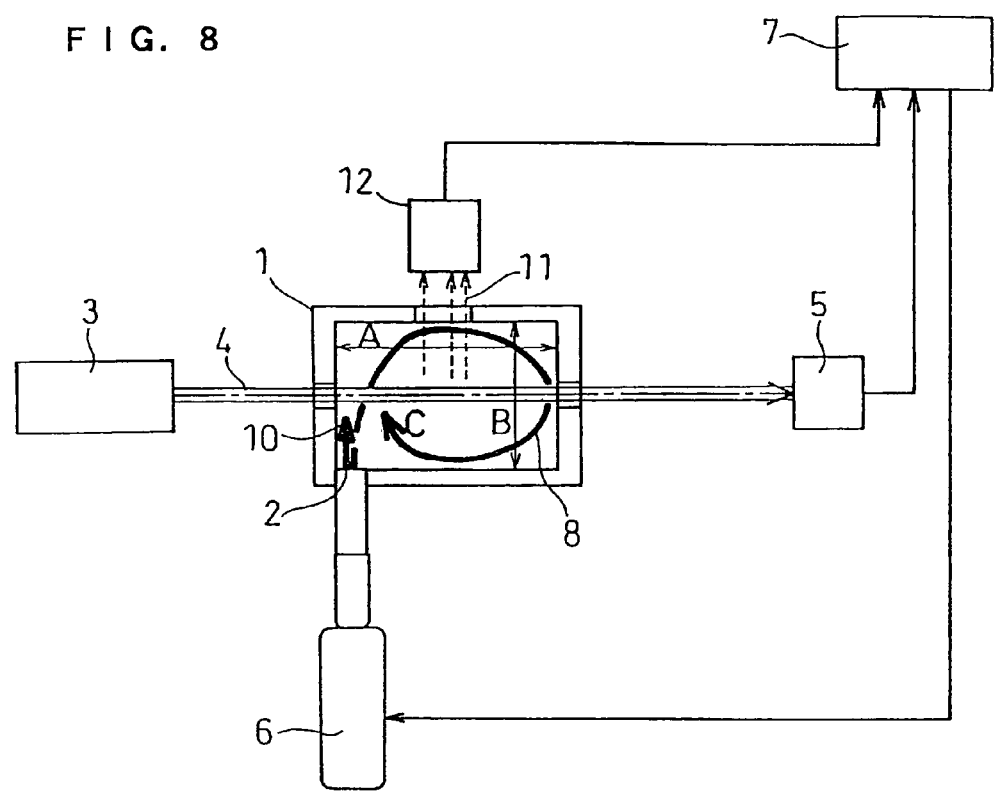
FIG. 8 is a top view of a solution concentration measuring apparatus according to Embodiment 2 of the present invention.
Figure 9:
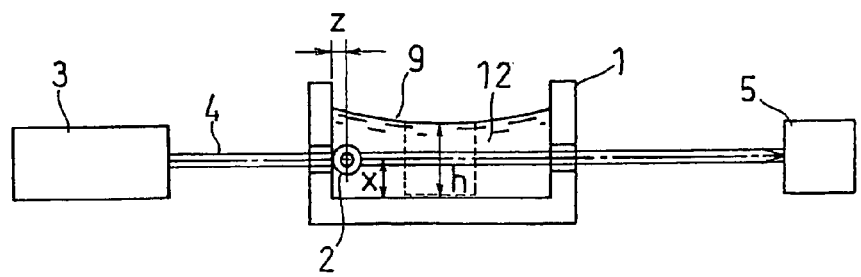
FIG. 9 is a partially cross-sectional side view of the solution concentration measuring apparatus according to Embodiment 2 of the present invention.

Referring now to FIGS. 8 and 9, Embodiment 2 of the present invention is described in detail below. In FIGS. 8 and 9, the constituent elements represented by reference characters 1 to 10 are the same as the constituent elements represented by reference characters 1 to 10 in FIGS. 1 and 2 used for describing the foregoing Embodiment 1, and they function in the same manner. It should be noted, however, that the light projected and scattered in a test liquid or a liquid mixture is detected in this embodiment.

Scattered light 11 that arises while the substantially parallel light 4 is propagated through a test liquid is detected by a photosensor 12. The output signal of the photosensor 12 corresponds to the intensity of the scattered light 11 and is analyzed by the computer 7.

In this embodiment, the concentration of protein in a test liquid is measured, using a solution containing protein as the test liquid and a reagent liquid of sulfosalicylic acid (a reagent obtained by dissolving sodium sulfate in an aqueous solution of 2-hydroxy-5-sulfobenzoic acid) as the reagent liquid. In this case, when the test liquid and the reagent liquid of sulfosalicylic acid are mixed together, the protein component of the test liquid coagulates, thereby making the resultant whole liquid mixture turbid. Thus, by measuring the degree of opacity, i.e., turbidity, the protein concentration can be determined. The turbidity is measured as the intensity of scattered light, i.e., the output signal of the photosensor 12. The higher the protein concentration, the higher the turbidity, and the greater the output signal of the photosensor 12.

In calculating the protein concentration, the turbidity of a standard solution of a known concentration, i.e., the output signal of the photosensor 12, is measured in advance, and based on this, a calibration curb is prepared. Then, the turbidity of a test liquid of an unknown concentration is measured, and the concentration is calculated by referring to the prepared calibration curb.

In this embodiment, the optical property, i.e., the property change in turbidity, is influenced not only by the stirring effect but also by the reaction (coagulation) property, unlike the foregoing Embodiment 1.

The operations of this embodiment were performed as follows:

First, an aqueous solution with a protein concentration of 100 mg/dl was introduced as a test liquid into the sample cell 1. At this time, the volume of the test liquid introduced was 0.25 ml. The computer 7 was started to record the output signal of the photosensor 12. The changes over time in the output signal of the photosensor 12 after the start of the recording following the introduction are shown by ● in FIG. 10.

In FIG. 10, the elapsed period of time since the start of measurement of the output signal is plotted in abscissa, and the output signal of the photosensor 12 is plotted in ordinate. At an elapsed time of 20 seconds since the start of the measurement, the computer 7 controlled the pump 6 so that 0.05 ml of the reagent liquid of sulfosalicylic acid was injected from the injection port 2 over 2 seconds.

Likewise, 0.25 ml of an aqueous solution with a protein concentration of 30 mg/dl, 10 mg/dl, or 0 mg/dl was introduced into the sample cell 1. At an elapsed time of 20 seconds since the start of the measurement, 0.05 ml of the reagent liquid of sulfosalicylic acid was injected. The output signals of the photosensor 12 for the aqueous solutions having the concentrations of 30 mg/dl, 10 mg/dl, and 0 mg/dl, respectively, are shown by ■, X, and ○ in FIG. 10.

In FIG. 10, the output signals as shown by ●,■, X, and ○ changed largely near the point when the reagent liquid was injected, and this was attributed to the invasion of the flux of the injected reagent liquid itself on the optical path of the substantially parallel light 4. This was because the refractive index of the protein aqueous solution, which is a test liquid, is different from that of the aqueous solution of sulfosalicylic acid, and hence, the resultant local unevenness caused a large change in the intensity of the scattered light. Further, this was also because the injection caused fine particles such as bubbles to enter the optical path, thereby causing a large change in the intensity of the scattered light. The region of this large change was shown by hatching. From the start of the measurement until the elapsed time of 20 seconds at which the injection was started, all of the respective solid lines and the dotted line coincided with one another, so this period was illustrated as only one solid line.

In calculating the concentration of a specific component of a test liquid, the computer 7 analyzes the output signal of the photosensor 12 after the mixing of the reagent liquid represented by this solid line, while referring to the previously prepared calibration curb, in order to calculate the concentration of the test liquid. In the above operations, since the same volume of the reagent liquid is injected into the same volumes of the test liquids over the same period of time, the homogenization by stirring proceeds in the same manner. However, as is clear from FIG. 10, it takes a different period of time for each output signal to reach saturation, i.e., to become stabilized. This is because the reaction speed is different according to the protein concentration.

In such cases, conventionally, the concentration was calculated, using a test liquid that required the longest period of time for the stabilization of the output signal. That is, in the case of a test liquid having a lowest protein concentration to be possibly detected, the output signal was measured at a point in time until which the output signal was expected to have been sufficiently stabilized, and the concentration of the test liquid was calculated using the measured output signal. Such a method has a problem of requiring a long measurement time even if the measurement can be completed within a short period of time because of high reaction speed. Further, in the case of high protein concentrations and high reaction speeds, if an unnecessarily long period of time elapses, the coagulated protein may start precipitating to cause a change in the intensity of scattered light, thereby impairing the accuracy. Also, since the reaction speed is dependent on temperature as well, there was a need to perform a measurement at a constant temperature.

Hence, in the following, this embodiment describes the method of the present invention that not only calculates the concentration but also determines the completion of a reaction, based on the output signal of the photosensor 12. This embodiment can set the measurement time necessary and sufficient, thereby enabling a substantial increase in measurement speed. In addition, this embodiment needs no temperature control and can prevent a degradation in accuracy due to the precipitation phenomenon and the like. In such cases as described above, sufficient completion of a reaction (the stability of the output signal) is determined based on the optical property of the solution (the output signal of the photosensor 12).

First, the maximum period of time within which a measurement is performed is set in advance. This period refers to the longest waiting period of time from the start of the measurement until obtaining the result, and if a measurement takes more than this maximum period of time, this measurement is rendered invalid. This pre-set period of time is referred to as a predetermined period of time T.

According to this method, homogenization is determined when the amount of change in an output signal S1 of the photosensor 12 per unit time, i.e., a derivative signal dS1/dt, has continuously been in a predetermined range R1 for a predetermined period of time T1 within the predetermined period of time T.

Specifically, homogenization is determined when dS1/dt [V/S] has continuously been in a predetermined range R1 represented by formula (2) for a predetermined period of time T1 (10 seconds) or longer within a predetermined period of time T (200 seconds) after the start of a measurement.

$$-1 \times 10^{-4} \leq dS1/dt \leq 1 \times 10^{-4} \quad (2)$$

Figure 11:
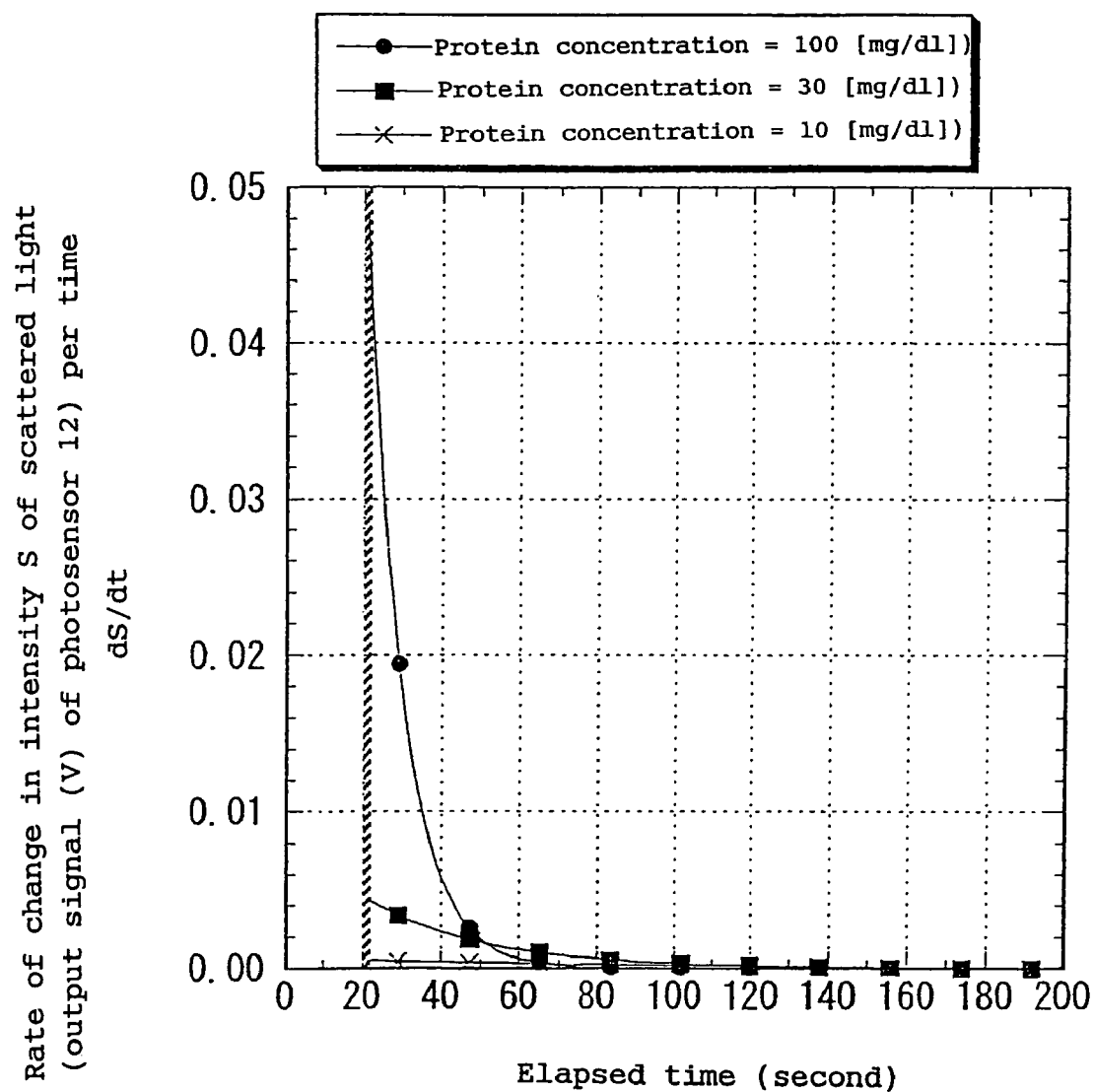
FIG. 11 is a graph showing the rate of change over time in the derivative signal of output signal of the photosensor 12 in Embodiment 2 of the present invention.

In FIG. 11, the derivative signal of output signal of the photosensor 12 was plotted in ordinate. ●, ■, and X of FIG. 11 correspond to the derivative signals represented by ●, ■, and X of FIG. 10, respectively. In FIG. 11, in the same manner as in FIG. 10, during the period of about 2 seconds or more from the elapsed time of 20 seconds at which the injection of the reagent liquid was started, the flux of the injected reagent liquid itself entered the optical path of the substantially parallel light 4. As a result, the intensity of the scattered light was disturbed, causing a violent change in the output signal of the photosensor 12. In FIG. 11, ○ was omitted, since it looks like substantially zero.

Since the details of FIG. 11 are not readable, a graph was prepared as FIG. 12 by enlarging the ordinate of FIG. 11 around 0 and enlarging the abscissa at 60 to 200 seconds. FIGS. 11 and 12 indicate that the derivative signal of output signal of the photosensor 12 was in the order of ●>■>X immediately after the injection of the reagent liquid, but after an elapsed time of about 120 seconds, this sequence was totally reversed, so that the derivative signal was in the order of X>■>●. Then, all of ●, ■, and X asymptotically approached zero.

For the condition for determining the completion of a reaction, a point of time when the derivative signal dS1/dt of output signal of the photosensor 12 has continuously been in the predetermined range R1 represented by formula (2) for the predetermined period of time T1 (10 seconds) or longer within the predetermined period of time T (200 seconds) after the start of a measurement was found from FIG. 12 as follows.

The derivative signal dS1/dt of output signal of the photosensor 12 became $1 \times 10^{-4}$ [V/S] or less from an elapsed time of 77 seconds for ●, from an elapsed time of 135 seconds for ■, and from an elapsed time of 166 seconds for X. After these points in time, since ●, ■, and X asymptotically approached zero, the derivative signal was in the predetermined range R1 as expressed by formula (2).

Therefore, in FIG. 12, if the point of the lapse of 10 seconds from the point when the derivative signal dS/dt fell within the predetermined range R1 expressed by formula (2) is within the predetermined period of time T (200 seconds) after the start of the measurement, the reaction could be determined as having been completed at an elapsed time of 200 seconds. Specifically, for ●, reaction completion could be determined at an elapsed time of 87 seconds. For ■, reaction completion could be determined at an elapsed time of 145 seconds. For X, reaction completion could be determined at an elapsed time of 176 seconds. By using the determination condition of the above example, it was possible to adequately determine whether or not the reaction had been completed.

In measuring the turbidity of a test liquid from the output signal of the photosensor 12 to calculate the protein concentration, the output signal of the photosensor 12 at the point when the reaction completion was determined may be analyzed, as described above. Specifically, for ●, the output signal of the photosensor 12 at the elapsed time of 87 seconds is used, and for ■, the output signal of the photosensor 12 at the elapsed time of 145 seconds is used. For X, the output signal of the photosensor 12 at the elapsed time of 176 seconds is used. In preparing a calibration curb, the same condition as described above may be used for preparation.

Figure 16:
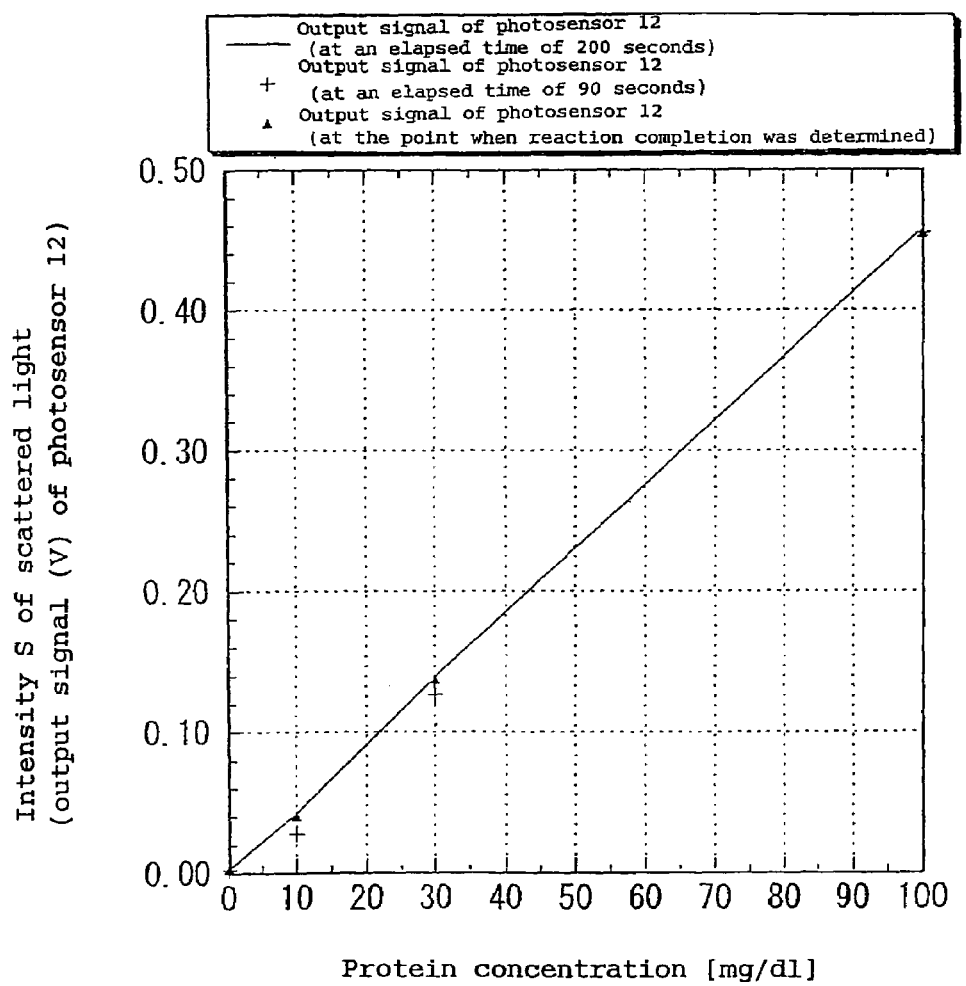
FIG. 16 is a graph showing the dependency of the output signal of the photosensor 12 used in Embodiments 2 to 3 of the present invention on the protein concentration.

FIG. 16 shows the dependency of the output signal of the photosensor 12 on the protein concentration. The solid line represents the output signal at an elapsed time of 200 seconds, and + represents the output signal at an elapsed time of 90 seconds. ▲ represents the output signal at the point when the reaction completion was determined under the above condition, i.e., the output signal at the elapsed time of 176 seconds for 10 mg/dl, the output signal at the elapsed time of 145 seconds for 30 mg/dl, and the output signal at the elapsed time of 87 seconds for 100 mg/dl. As can be seen from FIG. 16, in the case of the determination of reaction completion as represented by ▲, the accuracy was retained at the respective concentrations; however, in the case of the output signal at the elapsed time of 90 seconds as represented by +, the lower the concentration, the lower the accuracy.

As described above, according to this embodiment, the concentration can be measured in a necessary and sufficient measurement time while the accuracy is ensured, so that the measurement time can be shortened. Further, the degradation in accuracy due to insufficient completion of the reaction can be avoided.

It is needless to say that the condition for determining the completion of a reaction is not limited to the above-described condition. That is, T, T1, and the predetermined range R1 expressed by formula (2) may be set as appropriate, according to various conditions such as the kind of the reagent liquid, the injection speed, the arrangement of the optical system, the accuracy required, the measurement time, the calibration curb, etc. Also, in calculating the concentration of a specific component of a test liquid, the computer 7 analyzes the output signal of the photosensor 12 at the point when the reaction completion was determined, while referring to the pre-set calibration curb, in order to calculate the concentration of the test liquid. In preparing a calibration curb, the same condition as described above may be used for preparation. Also, it may be prepared by grasping the whole characteristics of changes over time in output signal responsive to standard solutions of known concentrations, which corresponds to FIG. 10, and using the output signal at the point when reaction completion was determined.

As described above, according to this embodiment, the degree of reaction completion can be determined with the sample cell mounted on the optical system. Further, since the time needed for a measurement is necessary and sufficient, time can be saved. Accordingly, while the process can be simplified, misoperations are unlikely to occur. These practical effects are extremely large, thereby making it possible to enhance the efficiency of measurements and tests and to achieve labor-savings thereof.

This embodiment has described an example in which the turbidity is measured by detecting, by means of the photosensor 12, the light that is scattered while the substantially parallel light 4 is propagated through the solution. However, when the turbidity is measured as the intensity of transmitted light (the output signal of the photosensor 5), the same operations are also possible, and highly accurate measurements can be realized in the same manner.

In this case, however, the higher the protein concentration, the higher the turbidity, and the smaller the output signal of the photosensor 5. Also, the derivative signal dS1/dt of output signal of the photosensor 5 asymptotically approached zero from minus values. In this way, when the reaction completion is determined using the intensity of transmitted light, T, T1, and the predetermined range R1 expressed by formula (2) may also be set as appropriate, according to various conditions such as the kind of the reagent liquid, the injection speed, the arrangement of the optical system, the accuracy required, the measurement time, the calibration curb, etc.

Also, the derivative signal of the output signal may be obtained with an analogue circuit, or, it may be obtained by measuring a plurality of times at appropriate intervals of time and performing differential analysis. In the above case, the output signal monotonously increased or monotonously decreased. However, even if it decreases in an oscillating manner or increases in an oscillating manner, the methods according to the present invention are applicable in the same manner.

Embodiment 3

In this embodiment, a different method of determining the completion of a reaction is described using the apparatus having the structure as illustrated in FIGS. 8 and 9 used in the foregoing Embodiment 2. In the same manner as in Embodiment 2, the output signal of the photosensor 12 as illustrated in FIGS. 10 and 16 was used to calculate and determine the concentration. However, unlike Embodiment 2, (dS1/dt)/S1 was used in this embodiment as an index to evaluate whether or not it was in a predetermined range R2.

In Embodiment 2, dS1/dt was used as the evaluation index. In this case, if S1 is relatively small, i.e., if the concentration of a test liquid is in a lower range, dS1/dt itself becomes small. Accordingly, in the case of a low concentration test liquid, the reaction may be mistakenly determined as having been completed even if the degree of reaction completion is low. Therefore, in this embodiment, the value obtained by dividing dS1/dt by the output signal S1, i.e., (dS1/dt)/S1, is used as the evaluation index to determine reaction completion.

First, the maximum period of time within which a measurement is performed is set in advance. This period refers to the longest waiting period of time from the start of a measurement until obtaining the result, and if a measurement takes more than this maximum period of time, this measurement is rendered invalid. This pre-set period of time is referred to as a predetermined period of time T.

According to this method, homogenization is determined when the value obtained by dividing the amount of change in an output signal S1 of the photosensor 12 per unit time by the output signal S1, i.e., (dS1/dt)/S1, has continuously been in a predetermined range R2 for a predetermined period of time T2 within the predetermined period of time T.

Specifically, the liquid mixture is determined as having been homogenized when (dS1/dt)/S1 [V/S] has continuously been in a predetermined range R2 represented by formula (3) for a predetermined period of time T2 (10 seconds) or longer, within a predetermined period of time T (200 seconds) after the start of a measurement.

$$-5 \times 10^{-4} \leq (dS1/dt)/S1 \leq 5 \times 10^{-4} \quad (3)$$

Figure 13:
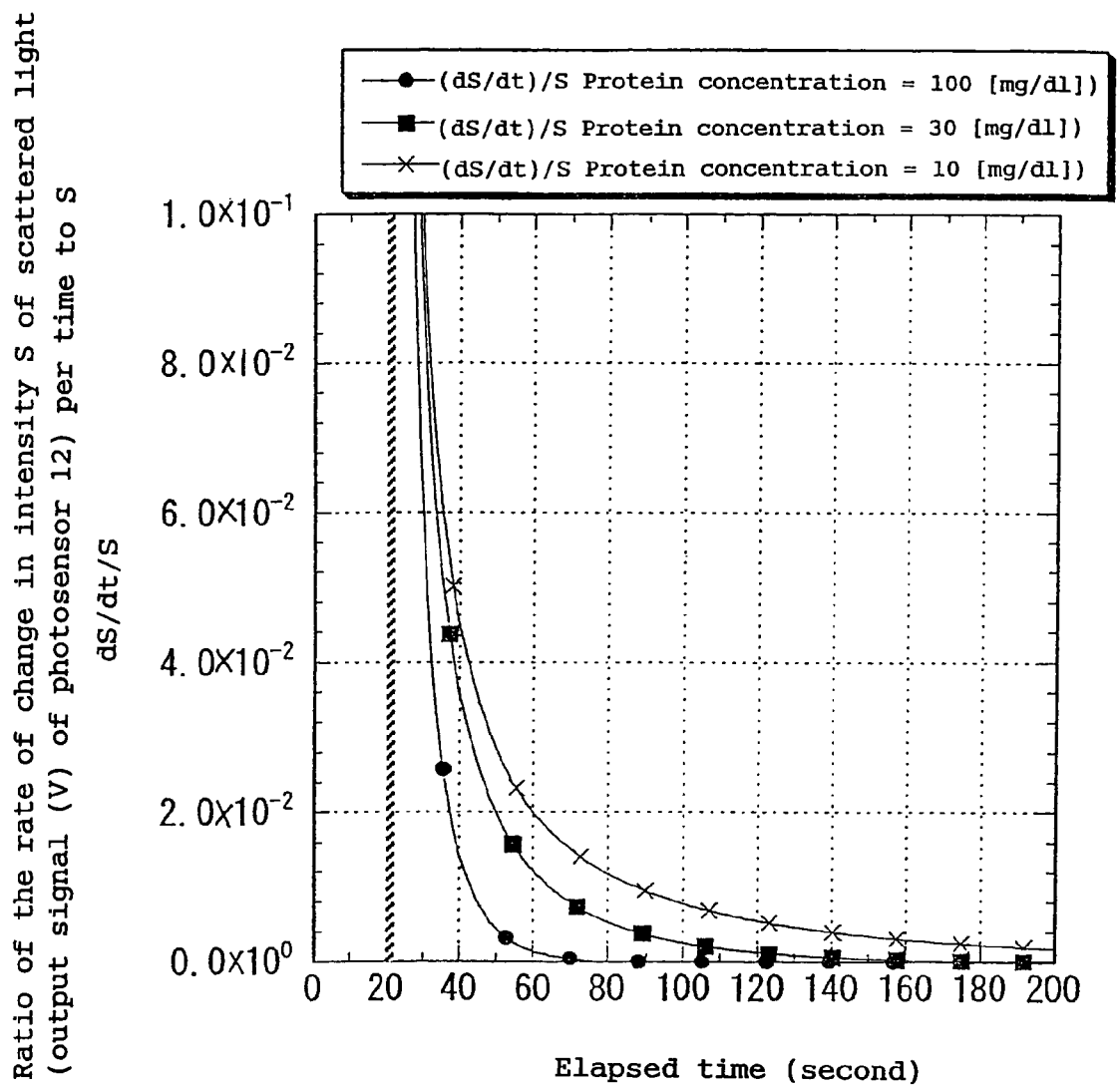
FIG. 13 is a graph showing the values obtained by dividing the derivative signal of output signal of a photosensor 12 of Embodiment 3 of the present invention by the output signal.
Figure 14:
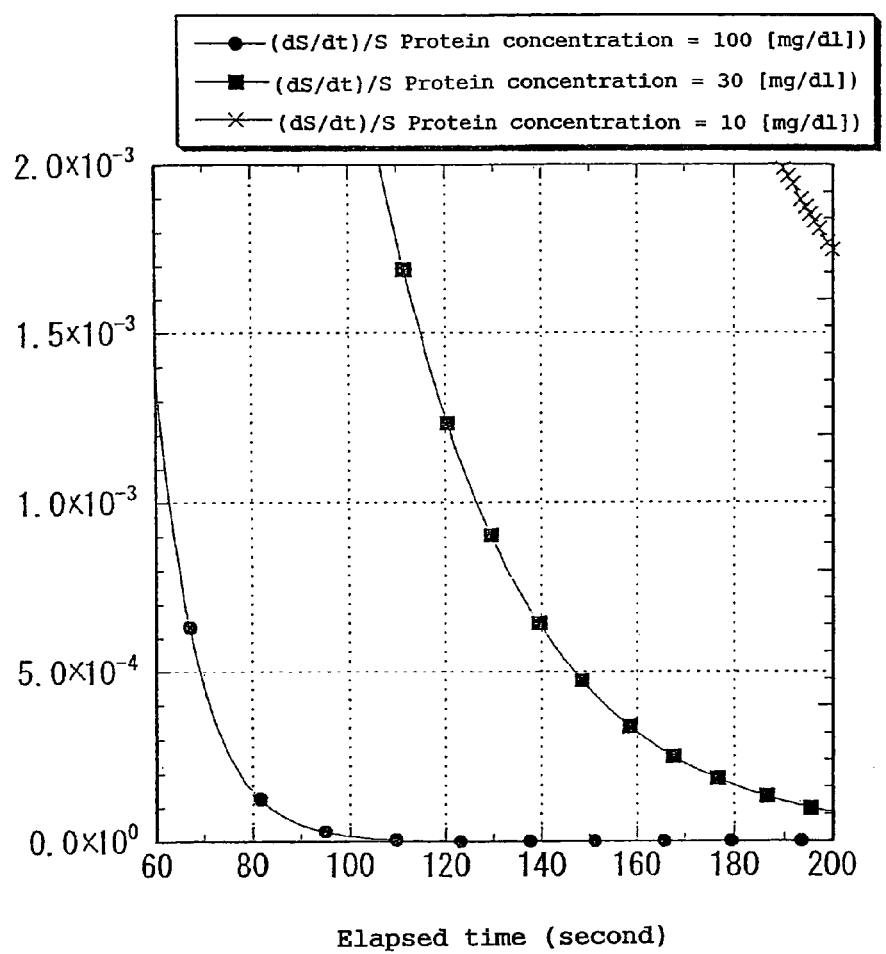
FIG. 14 is a graph obtained by enlarging the ordinate around 0 and enlarging the abscissa around 60 to 200 seconds in FIG. 13.

In FIG. 13, the value obtained by dividing the derivative signal of output signal of the photosensor 12 by the output signal is plotted in ordinate. ●, ■, and X of FIG. 13 correspond to the values obtained by dividing the derivative signals represented by ●, ■, and X of FIG. 10, respectively, by the output signals. In FIG. 13, in the same manner as in FIG. 10, during the period of about 2 seconds or more from the elapsed time of 20 seconds at which the injection of the reagent solution was started, the flux of the injected reagent liquid itself entered the optical path of the substantially parallel light 4, so that the intensity of scattered light was disturbed. As a result, (dS1/dt)/S1 changed violently. In FIG. 13, ○ was omitted, since it looks like substantially zero. Since the details of FIG. 13 are not readable, FIG. 14 was prepared by enlarging the ordinate around 0 and enlarging the abscissa around 60 to 200 seconds. FIGS. 13 and 14 show that the derivative signal of output signal of the photosensor 12 was in the order of X>■>● immediately after the injection of the reagent liquid, and that they asymptotically approached zero.

For the condition for determining the completion of a reaction, a point of time when the derivative signal dS1/dt/S1 has continuously been in the predetermined range R2 represented by formula (3) for the predetermined period of time T1 (10 seconds) or longer within the predetermined period of time T (200 seconds) after the start of a measurement was found from FIG. 14 as follows.

(dS1/dt)/S1 became $5 \times 10^{-4}$ [V/S] or less from an elapsed time of 69 seconds for ● and from an elapsed time of 148 seconds for ■. However, for X, even after an elapsed time of 200 seconds, (dS1/dt)/S1 did not fall to $5 \times 10^{-4}$ [V/S] or less. After 200 seconds, ● and ■ asymptotically approached zero, being in the predetermined range R3 as expressed by formula (3). Therefore, if the point of the lapse of 10 seconds from the point when it fell within the predetermined range expressed by formula (3) is within the predetermined period of time T (200 seconds) after the start of the measurement, the reaction could be determined as having been completed at the point of 200 seconds.

Specifically, for ●, the reaction could be determined as having been completed at an elapsed time of 79 seconds. For ■, the reaction could be determined as having been completed at an elapsed time of 158 seconds. For X, however, since the reaction could not be determined as having been completed, this measurement was rendered invalid. Accordingly, as is clear from FIG. 16, when the protein concentration is 10 mg/dl, the accuracy is low, but such measurement could be rendered invalid. In the foregoing Embodiment 2, even when the accuracy is poor in such a low concentration range, the reaction is determined as having been completed, and such a measurement is rendered valid, so that the reliability of the measurement may be impaired. In this embodiment, however, by making such measurements invalid, the reliability can be secured.

As described above, according to this embodiment, the concentration can be measured in a necessary and sufficient measurement time while the accuracy is ensured, so that the measurement time can be shortened. Further, it is possible to detect the degradation in accuracy due to relatively insufficient completion of the reaction which may occur when the test liquid is in a low concentration range, so that the reliability can be improved.

It is needless to say that the condition for determining the completion of a reaction is not limited to the above-described condition. That is, T, T2, and the predetermined range R2 expressed by formula (3) may be set as appropriate, according to various conditions such as the kind of the reagent liquid, the injection speed, the arrangement of the optical system, the accuracy required, the measurement time, the calibration curb, etc.

Embodiment 4

This embodiment uses the apparatus having the same structure as that illustrated in FIGS. 8 and 9 used in the foregoing Embodiment 3, but employs a different method of determining the completion of a reaction. In the same manner as in Embodiment 3, the output signal of the photosensor 12 as illustrated in FIGS. 10 and 16 is used to calculate and determine the concentration. However, unlike Embodiment 3, this embodiment also uses an output signal S0 of the photosensor 12 before the injection of the reagent liquid. Also, in order to facilitate the understanding of S1 values, FIG. 15 showed a graph in which the ordinate of FIG. 12 is expressed logarithmically.

Specifically, instead of the S1 used in Embodiments 2 and 3, S1−S0 is used as an evaluation index. That is, (d(S1−S0)/dt)/(S1−S0) is used as the index. However, since S0 is evaluated as being independent of time, the equation d(S1−S0)/dt=dS1/dt holds, and whether or not (dS1/dt)/(S1−S0) is in a predetermined range R3 is evaluated.

Therefore, homogenization and/or reaction completion is determined when (dS1/dt)/(S1−S0) has been in the predetermined range R3 for a predetermined period of time T3 within a predetermined period of time T.

Except for the above differences, this method is the same as that of Embodiment 3. Accordingly, it is possible to detect the relative degradation in accuracy in the case of using a low-concentration test liquid, as described in Embodiment 3, without being influenced by the turbidity of the test liquid before the injection of the reagent liquid.

As described above, this embodiment can detect the degradation in accuracy due to relatively insufficient completion of the reaction which may occur in the case of a low-concentration-range test liquid, without being influenced by the turbidity of the test liquid itself, so that the reliability can be further improved.

Embodiment 5

Figure 17:
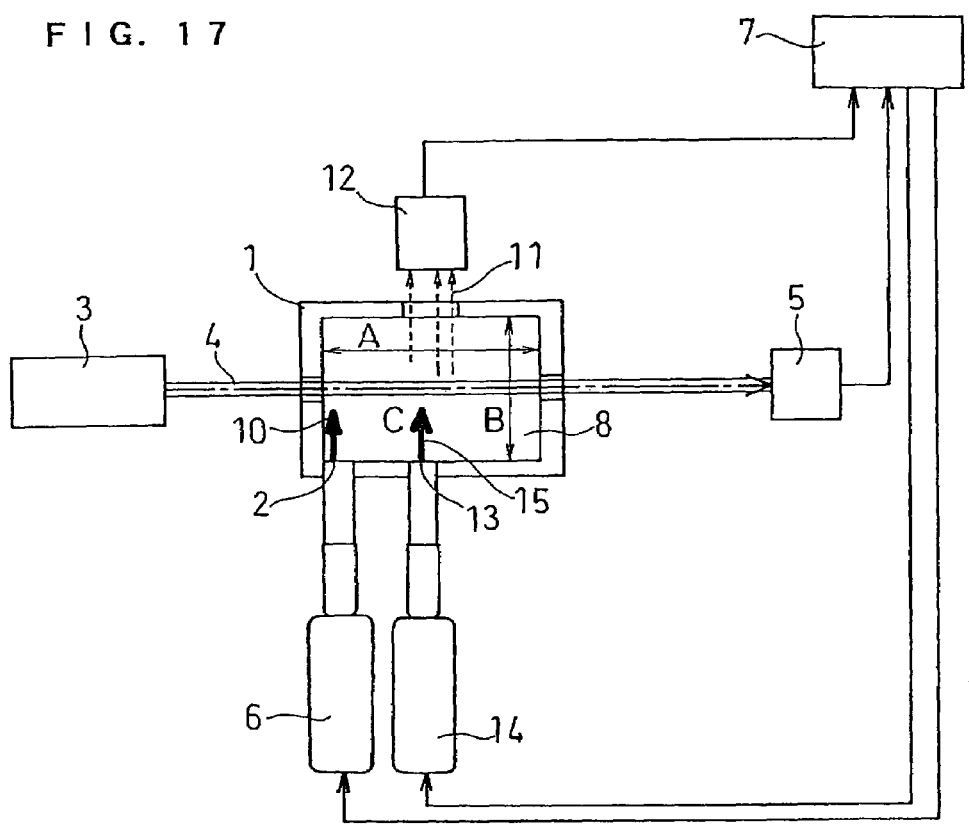
FIG. 17 is a top view of a solution concentration measuring apparatus according to Embodiment 5 of the present invention.

Referring now to FIG. 17, Embodiment 5 of the present invention is described in detail below. In FIG. 17, the constituent elements represented by reference characters 1 to 12 are the same as the constituent elements represented by reference characters 1 to 12 in FIG. 8, and they function in the same manner. Like the injection port 2, an injection port 13 is disposed in the side face of the sample cell 1 having no optical window and has an internal diameter (diameter) of 0.1 cm. A pump 14 injects a reagent liquid into a test liquid in the sample cell 1 from the injection port 13. Also, an arrow 15 indicates the injection direction in which the reagent liquid is injected from the injection port 13. In this embodiment, more than one kind of reagent liquid or the like is injected. For example, a buffer solution is first injected into the test liquid in the sample cell 1, and then, an antibody reagent liquid or the like is injected.

Figure 18:
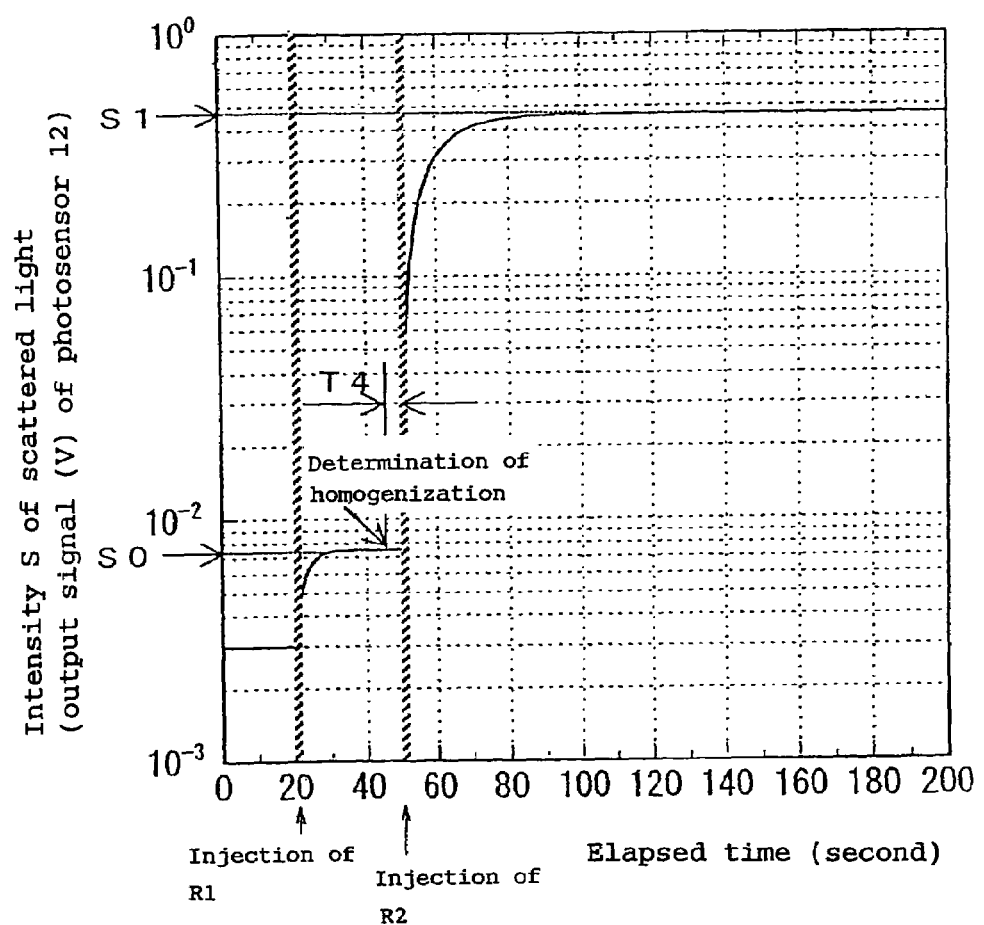
FIG. 18 is a graph showing the changes over time in the output signal of a photosensor 12 in Embodiment 5 of the present invention.

In this embodiment, following the injection of the buffer solution, which is a first reagent liquid, after the first reagent liquid and the test liquid are determined as having been homogenized, the optical property of the liquid mixture is measured. Subsequently, the antibody reagent liquid, which is a second reagent liquid, is injected, and after the completion of the reaction, the optical property of the liquid mixture is measured, to determine the concentration. In the following, a method of determining homogenization and determining reaction completion according to the methods described in Embodiments 1 to 4 is described with reference to FIG. 18.

First, urine samples (test liquids) having human serum albumin concentrations of 0.1 mg/dl, 0.3 mg/dl, 1.0 mg/dl, and 3.0 mg/dl were prepared by adding human serum albumin to urine from which human serum albumin was not detectable (substantially zero concentration). Also, a 0.05 M MOPS buffer solution was prepared as the first reagent solution (R1). Then, an antibody reagent liquid (R2) was prepared as the second reagent liquid by purifying the antibody component of antihuman albumin rabbit serum.

Thereafter, 0.2 ml of each test liquid was introduced into the sample cell 1, at which point the photosensor 12 started measuring the intensity of scattered light (elapsed time of 0 seconds). At an elapsed time of 20 seconds, the buffer solution serving as the first reagent solution (R1) was injected over 2 seconds. Then, using the method described in any of the above-mentioned embodiments, the first reagent liquid and the test liquid were determined as having been homogenized. At the point when homogenization was determined, the optical property of the liquid mixture was measured. Upon the lapse of a predetermined period of time T4 from the point when homogenization was determined, the antibody reagent liquid serving as the second reagent liquid was injected over 2 seconds. In other words, during the period of time from the point when homogenization was determined until the lapse of the predetermined period of time T4, the optical property of the liquid mixture was measured to obtain an output signal S0. Then, using the method described in any of the above-mentioned embodiments, the reaction associated with the second reagent liquid was determined as having been completed, and then the optical property of the liquid mixture was measured to obtain an output signal S1. It was confirmed that the difference between S0 and S1 thus obtained was proportional to the human serum albumin concentration of the test liquid.

Likewise, in the case of using more than two kinds of reagent liquids, each reagent liquid is injected, and after the lapse of a predetermined period of time from the point of the determination of homogenization or reaction completion, the next reagent liquid is injected. In each stage, after the point of the determination of homogenization or reaction completion and before the injection of the next reagent liquid, the optical property is measured if necessary, and the concentration is calculated based on the measured value.

As described above, according to this embodiment, the optical property is measured after determining homogenization and/or reaction completion following the injection of each reagent liquid, and thereafter, the next reagent liquid is injected. Therefore, the respective impacts of the reagent liquids can be distinguished in making measurements, thereby resulting in high reliability. For example, in measuring the concentration of a specific antigen in a test liquid, the turbidity may be measured by mixing the test liquid and a buffer solution in advance and then mixing an antibody reagent liquid. In this case, the turbidity due to the antibody-antigen combination, which is a specific binding reaction, can be distinguished from the turbidity of the test liquid itself and the turbidity resulting from the mixing of the test liquid and the buffer solution in making measurements. Accordingly, only the specific antigen can be specifically detected, and hence, the reliability of measurements can be ensured. It should be noted that the predetermined period of time T4 is zero or more, and that it may be any period of time during which the optical property can be measured.

INDUSTRIAL APPLICABILITY

As described above, the present invention needs only a period of time necessary for homogenization and/or completion of a reaction. That is, the invention only requires that the necessary condition be satisfied with respect to the measurement time. Therefore, the measurement time can be shortened, which is highly practically effective, and more efficient and labor-saving measurements and tests become possible. Further, since measurements with poor accuracy can be rendered invalid, the reliability is high. Also, the concentration can be measured by specifically detecting only a specific component of a test liquid, which is greatly practically effective. The invention is applicable to, for example, urinalysis.

The invention claimed is:

1. A method for determining homogenization and/or reaction completion, comprising the steps of:
   (1) mixing a test liquid and a reagent liquid to obtain a liquid mixture;
   (2) measuring an optical property of said liquid mixture after the mixing continuously or a plurality of times discretely;
   (3) obtaining a relation between the measured value of the optical property obtained and the elapsed period of time since the start of the measurement after the mixing; and
   (4) determining, on the basis of said relation, whether said test liquid and said reagent liquid have been substantially homogeneously mixed with each other and/or a reaction between said test liquid and said reagent liquid has been substantially completed, wherein
   said step (3) is a step of obtaining $(dS1/dt)/S1$ (wherein $S1$ is the measured value of the optical property obtained and $T$ is the elapsed period of time since the start of the measurement after the mixing), and
   said step (4) is a step of determining that said test liquid and said reagent liquid have been substantially homogeneously mixed with each other and/or the reaction between said test liquid and said reagent liquid has been substantially completed, when the $(dS1/dt)/S1$ has continuously been in a predetermined range $R2$ for a predetermined period of time $T2$ or longer.

2. The method for determining homogenization and/or reaction completion in accordance with claim 1, wherein a measurement is rendered invalid when homogenization and/or reaction completion has not been determined within a predetermined period of time $T$ from the start of the measurement.

3. A method for determining homogenization and/or reaction completion, comprising the steps of:
   (1) mixing a test liquid and a reagent liquid to obtain a liquid mixture;
   (2) measuring an optical property of said test liquid and said liquid mixture continuously, or, measuring an optical property of said test liquid at least once and measuring an optical property of said liquid mixture after the mixing a plurality of times discretely;
   (3) obtaining a relation between the measured value of the optical property obtained and the elapsed period of time since the start of the measurement after the mixing; and
   (4) determining, on the basis of said relation, whether said test liquid and said reagent liquid have been substantially homogeneously mixed with each other and/or the reaction between said test liquid and said reagent liquid has been substantially completed, wherein
   said step (3) is a step of obtaining $(dS1/dt)/(S1-S0)$ (wherein $S0$ is the measured value of the optical property of said test liquid, $S1$ is the measured value of the optical property of said liquid mixture, and $T$ is the elapsed period of time since the start of the measurement after the mixing), and
   said step (4) is a step of determining that said test liquid and said reagent liquid have been substantially homogeneously mixed with each other and/or the reaction between said test liquid and said reagent liquid has been substantially completed, when the $(dS1/dt)/(S1-S0)$ has continuously been in a predetermined range $R3$ for a predetermined period of time $T3$ or longer.

4. The method for determining homogenization and/or reaction completion in accordance with claim 3, wherein a measurement is rendered invalid when homogenization and/or reaction completion has not been determined within a predetermined period of time $T$ from the start of the measurement.

5. A method for measuring solution concentration, comprising the steps of:
   (1) mixing a test liquid and a reagent liquid to obtain a liquid mixture;
   (2) measuring an optical property of the liquid mixture after the mixing continuously or a plurality of times discretely;
   (3) obtaining a relation between the measured value of the optical property obtained and the elapsed period of time since the start of the measurement after the mixing;
   (4) determining, on the basis of said relation, whether said test liquid and said reagent liquid have been substantially homogeneously mixed with each other and/or a reaction between said test liquid and said reagent liquid has been substantially completed; and
   (5) determining the concentration of a specific component of said test liquid based on said measured value, wherein
   said step (3) is a step of obtaining $(dS1/dt)/S1$ (wherein $S1$ is the measured value of the optical property obtained and $T$ is the elapsed period of time since the start of the measurement after the mixing), and
   said step (4) is a step of determining that said test liquid and said reagent liquid have been substantially homogeneously mixed with each other and/or the reaction between said test liquid and said reagent liquid has been substantially completed, when the $(dS1/dt)/S1$ has continuously been in a predetermined range $R2$ for a predetermined period of time $T2$ or longer.

6. The method for measuring solution concentration in accordance with claim 5, further comprising the step of mixing another reagent liquid with said test liquid, after determining that the said test liquid and said reagent liquid have been homogeneously mixed and/or the reaction therebetween has been substantially completed.

7. The method for measuring solution concentration in accordance with claim 6, wherein another reagent liquid is mixed with said test liquid upon the lapse of a predetermined period of time $T4$ after determining that the said test liquid and said reagent liquid have been homogeneously mixed and/or the reaction therebetween has been substantially completed, and the optical property of said liquid mixture is measured prior to the lapse of the predetermined period of time $T4$.

8. The method for measuring solution concentration in accordance with claim 5, wherein a measurement is rendered invalid when homogenization and/or reaction completion has not been determined within a predetermined period of time T from the start of the measurement.

9. A method for measuring solution concentration, comprising the steps of:
- (1) mixing a test liquid and a reagent liquid to obtain a liquid mixture;
- (2) measuring an optical property of said test liquid and said liquid mixture continuously, or, measuring an optical property of said test liquid at least once and measuring an optical property of said liquid mixture after the mixing a plurality of times discretely;
- (3) obtaining a relation between the measured value of the optical property obtained and the elapsed period of time since the start of the measurement after the mixing;
- (4) determining, on the basis of said relation, whether said test liquid and said reagent liquid have been substantially homogeneously mixed with each other and/or a reaction between said test liquid and said reagent liquid has been substantially completed; and
- (5) determining the concentration of a specific component of said test liquid based on said measured value, wherein
said step (3) is a step of obtaining $(dS1/dt)/(S1-S0)$ (wherein S0 is the measured value of the optical property of said test liquid, S1 is the measured value of the optical property of said liquid mixture, and T is the elapsed period of time since the start of the measurement after the mixing), and said step (4) is a step of determining that said test liquid and said reagent liquid have been substantially homogeneously mixed with each other and/or the reaction between said test liquid and said reagent liquid has been substantially completed, when the $(dS1/dt)/(S1-S0)$ has continuously been in a predetermined range R3 for a predetermined period of time T3 or longer.

10. The method for measuring solution concentration in accordance with claim 9, further comprising the step of mixing another reagent liquid with said test liquid, after determining that the said test liquid and said reagent liquid have been homogeneously mixed and/or the reaction therebetween has been substantially completed.

11. The method for measuring solution concentration in accordance with claim 10, wherein another reagent liquid is mixed with said test liquid upon the lapse of a predetermined period of time T4 after determining that the said test liquid and said reagent liquid have been homogeneously mixed and/or the reaction therebetween has been substantially completed, and the optical property of said liquid mixture is measured prior to the lapse of the predetermined period of time T4.

12. The method for measuring solution concentration in accordance with claim 9, wherein a measurement is rendered invalid when homogenization and/or reaction completion has not been determined within a predetermined period of time T from the start of the measurement.

* * * * *